(12) United States Patent
Chi

(10) Patent No.: US 12,290,270 B2
(45) Date of Patent: May 6, 2025

(54) METHODS AND SYSTEMS FOR BONE MOUNTED ROBOTIC-ASSISTED HIP AND SHOULDER SURGICAL SYSTEMS

(71) Applicant: Unik Orthopedics, Inc, San Jose, CA (US)

(72) Inventor: Charlie Wen-Ren Chi, Milpitas, CA (US)

(73) Assignee: Unik Orthopedics, Inc., San Jose, CA (US)

( * ) Notice: Subject to any disclaimer, the term of this patent is extended or adjusted under 35 U.S.C. 154(b) by 0 days.

(21) Appl. No.: 18/391,245

(22) Filed: Dec. 20, 2023

(65) Prior Publication Data

US 2024/0122610 A1    Apr. 18, 2024

Related U.S. Application Data

(63) Continuation of application No. 17/546,626, filed on Dec. 9, 2021, now Pat. No. 11,890,023.

(60) Provisional application No. 63/124,697, filed on Dec. 11, 2020.

(51) Int. Cl.
| | |
|---|---|
| *A61B 17/17* | (2006.01) |
| *A61B 34/10* | (2016.01) |
| *A61B 34/30* | (2016.01) |
| *A61B 90/00* | (2016.01) |

(52) U.S. Cl.
CPC ...... *A61B 17/1742* (2013.01); *A61B 17/1703* (2013.01); *A61B 34/10* (2016.02); *A61B 34/30* (2016.02); *A61B 90/06* (2016.02); *A61B 2034/108* (2016.02); *A61B 2090/066* (2016.02)

(58) Field of Classification Search
CPC ......... A61B 34/10; A61B 34/20; A61B 34/30; A61B 34/32; A61B 34/76; A61B 90/06; A61B 17/1666; A61B 17/1746; A61B 17/1778; A61B 17/175
See application file for complete search history.

(56) References Cited

U.S. PATENT DOCUMENTS

2014/0276867 A1* 9/2014 Kelley ............... A61B 17/1746
623/22.32

* cited by examiner

*Primary Examiner* — Samuel S Hanna
(74) *Attorney, Agent, or Firm* — Polsinelli PC; Derek D. Donahoe

(57) ABSTRACT

Aspects of present disclosures involve systems, methods, and apparatus for a bone mounted robotic-assisted orthopedic surgery system for precise implant position, soft tissue balancing, and guidance of tools during a surgical procedure, particularly partial or total knee replacement procedure. The system features a bone-mounted robotic arm with an end-effector for precise positioning of a surgical tool, positioning of implants, and balancing of soft tissues. The reconfigurable robotic system requires minimal training by surgeons, is intuitive to use similar to conventional instrumented surgery, and has a small footprint. The system works with existing, conventional instruments, patient-specific instruments, sensor-assisted systems, and computer-assisted systems and does not require increased surgical time and safely provides the enhanced precision achievable by robotic-assisted systems and computer-assisted technologies.

15 Claims, 37 Drawing Sheets

Line BC is equal to Line AC
Line BD is equal to Line AD
Angle BCD is equal to Angle ACD

2406

2407

METHODS AND SYSTEMS FOR BONE MOUNTED ROBOTIC-ASSISTED HIP AND SHOULDER SURGICAL SYSTEMS

CROSS-REFERENCE TO RELATED APPLICATION

This application is a continuation of patent application Ser. No. 17/546,626 entitled "METHODS AND SYSTEMS FOR BONE MOUNTED ROBOTIC-ASSISTED HIP AND SHOULDER SURGICAL SYSTEMS" that was filed on Dec. 9, 2021, and is related to and claims priority under 35 U.S.C. § 119(e) from U.S. Patent Application No. 63/124,697, filed Dec. 11, 2020 entitled "METHODS AND SYSTEMS FOR BONE MOUNTED ROBOTIC-ASSISTED HIP AND SHOULDER SURGICAL SYSTEMS," the entire contents of both of which are incorporated herein by reference for all purposes.

TECHNICAL FIELD

Aspects of the present disclosure generally relate to systems and methods for creating and manufacturing customized surgical guides. More specifically, the present disclosure relates to methods for creating bone mounted guides customized to a particular patient from one or more two-dimensional images of a patient's hip or shoulder taken from an imaging device.

BACKGROUND

Through repeated heavy lifting, traumatic events, bone disease and/or arthritis, a patient's joints, such as the knee, hip, shoulder, and ankle may become degenerated, damaged or loosened to the point that pain or paralysis does not respond to medication or other forms of non-surgical treatments. One type of surgical procedure to address the patient's pain or deformity is total or partial joint arthroplasty.

A joint replacement procedure involves removing parts of an arthritic or damaged joint and replaced with a metal, plastic, or ceramic device called a prosthesis. The prosthesis or artificial joint is designed to replicate the movement of a normal, healthy joint. For example, the damaged hip joint is replaced with a metal ball attached to a metal stem that is fitted into the femur (the upper end of the femur), and a plastic liner with a metal socket is implanted into the pelvis, replacing the damaged acetabulum. Also, components that are properly positioned and oriented can achieve stability without impingement or loosening. Hip dislocation is one of the common complications after hip replacement surgery. An accurate component position is more likely to have an increased range of motion and stability and decreased pain. All of these factors helps minimize the need for revision surgery or prolonged rehabilitation.

One of the goals of computer-assisted robotic surgery (CARS) is to improve the accuracy, efficiency, and clinical outcome of a given orthopedic procedure compared to conventional methods. Current methods of robotic-assisted orthopedic surgery have some advantages in terms of accuracy and precision, surgical efficiencies, operative time, minimally invasiveness, and cost-effectiveness. One of the main disadvantages is the technological complexity compared to conventional surgery, which leads to a large increase in potential sources of error in terms of accuracies. Some of these technological errors may be difficult for the inexperienced surgeon to recognize; therefore, poor outcomes may occur if the technology is relied up on by the robot technician or blindly. Other disadvantages of robot-assisted surgery relative to conventional instrumentation methods include the cost of training for the entire surgical team, the time-consuming and steep learning curve associated with the adoption of new technology, and the high cost of the robotic surgical system itself, including the robot, computer equipment, software licenses, and disposable instruments and accessories.

Further, additional advantages are gained through the user of bone-mounted surgical robots compared to computer navigation and floor (fixed or free-standing) or bed-mounted robots. Some advantages include light and compact design based on surgical technique and instrumentation, small workspace near the surgical site, rigid attachment to the bone and different fixtures based on the surgical procedure or technique, less expensive, and precise positioning and orientation concerning the target implant. In addition, bone-mounted surgical robots are less susceptible to external forces, such as patient motion or bumping into the robot, compared with large free-standing robots which require the patient's anatomy to be immobilized to the operating table or by tracking patient and robot movement in real-time It is with these observations in mind, among others, that aspects of the present disclosure were conceived.

SUMMARY

In one embodiment in accordance with aspects of the disclosure, a method for performing a hip arthroplasty procedure. The method may include the operations of mating a registration guide to an anatomy of a patient, the registration guide customized to the anatomy of the patient by locating a plurality of landmark locations within a plurality of two-dimensional images of the patient's anatomy, the plurality of landmark locations defining an oriented workspace for a joint arthroplasty procedure and establishing, based on a position and orientation of the customized registration guide, a default position and orientation of an implant for use in the joint arthroplasty procedure, the position and orientation of the customized registration guide defining the oriented workspace for the joint arthroplasty procedure. The method may also include the operation of positioning a configurable bone-mounted robotic-assisted system in the oriented workspace for the joint arthroplasty procedure, the robotic-assisted system comprising a robot controller in communication with a bone-mounted robotic device, an acetabular reamer connected to a motor controlled by a motor controller, and a torque sensor in communication with the robot controller.

In another embodiment in accordance with aspects of the disclosure, a system for performing a surgical arthroplasty procedure may include a configurable bone-mounted robotic device attached to an anterior inferior iliac spine of a patient's anatomy via at least one guide pin, the orientation of the guide pin based on a drill guide of a customized registration guide defining an oriented workspace for the surgical arthroplasty procedure and generated from locating a plurality of landmark locations within a plurality of two-dimensional images of the patient's anatomy, the plurality of landmark locations defining the oriented workspace for the surgical arthroplasty procedure. The system may also include an acetabular reamer connected to a motor controlled by a motor controller and positioned within the oriented workspace for the surgical arthroplasty procedure by the configurable bone-mounted robotic device, a force sensor in mechanical communication with the acetabular reamer, and a computing device. The computing device may comprise at least one processing device and a non-transitory memory device in communication with the at least one processing device for storing one or more instructions that, when executed by the at least one processing device, cause the computing device to receive force information from the force sensor and adjust, based on the received force information, a position of the bone-mounted robotic device.

In yet another embodiment in accordance with aspects of the disclosure may include an implant jig for positioning a bone-mounted robotic-assisted device in relation to a patient's hip. The implant jig may include a substrate including a circular portion defining a handle of the implant jig, a first circular mating shape extending from the circular portion and oriented to contact a pubic portion of a rim of an acetabular portion of the patient's hip when the implant jig is positioned for a hip arthroplasty procedure, a second circular mating shape extending from the circular portion and oriented to contact an ischial portion of the rim of the acetabular portion of the patient's hip when the implant jig is positioned for the hip arthroplasty procedure, and a third circular mating shape extending from the circular portion and oriented to contact an ischium portion of the rim of the acetabular portion of the patient's hip when the implant jig is positioned for the hip arthroplasty procedure. The implant jig may also include a triangular portion comprising one or more drill hole guides extending outward from the triangular portion, the one or more drill holes for attaching at least one guide pin to an anterior inferior iliac spine of the patient's hip, the guide pin defining an oriented workspace for the hip arthroplasty procedure.

The present disclosure generally relates to system and methods for a bone-mounted robotic-assisted surgical system for treating patients suffering from joint disorders. For ease of discussion, the present disclosure is focused on hip replacement procedures, but can be applied to other joints, such as the knee, elbow, and ankle, as well as spinal procedures such as fusions. Some of the most common type of hip/shoulder procedures include total hip/shoulder replacement, partial hip/shoulder replacement or hip/shoulder resurfacing, trauma such as hip/shoulder fractures, osteotomies, and revision hip/shoulder surgery.

One aspect of the present disclosure may provide a bone-mounted robotic system for assisting total and partial hip/shoulder procedures in reaming the patient's acetabular/glenoid replaced by prosthesis of the same joint. The advantages of a bone-mounted robotic-assisted surgery system compared to a free-standing or bed-mounted surgical robot are such that once intra-operative registration is completed, motion tracking is not required since the robot moves with the patient's joint. Besides, the size and complexity of the robot are reduced as the robot is designed for a particular workspace of each joint procedure rather than a general robot that can perform different procedures. Smaller and less expensive robotic-assisted surgery systems are attractive for many reasons, including cost, ease of use, faster learning curve, less training required for the entire surgery staff, and space limitations due to smaller operating rooms, such as ambulatory surgery centers (ASCs).

Another aspect of the present disclosure may provide a method and system for mounting the robotic-assisted surgical system to the patient's anatomy. Mounting the robot on the patient's bone based on a target implant size, orientation, and position can be accomplished using a customized patient registration device. The registration device provides the implant's position and orientation in three-dimensional space relative to the patient's anatomy, pre-operative imaging data, and intra-operative robot. Manual instruments can also be used with the customized patient device in place of the robot for reaming or resection of bone using a saw guide.

In another aspect of the present disclosure, a bone-mounted robotic surgical system may be provided with torque/force sensors, a mechanical fixture with docking system, and electromechanical systems, such as power tools and motors for manual reaming or automated milling operations based on a specific toolpath, as well as feedback and control using sensors. After the implant position has been determined pre-operatively using the surgical planning software, the desired position and orientation can be transmitted to the robot either through a wired or wireless connection. Once the patient registration is complete, the initial position and orientation of the bone-mounted robot can be registered and secure to the patient's acetabulum using fixation pins and stabilized using additional support structures similar to a tripod.

Yet another aspect of the present disclosure may provide a robotic-assisted surgical system used during a joint replacement procedure. The system may include a robot including computer and computer networks, controllers, transceivers for communication, power systems, and other apparatus, such as power tools, monitoring equipment, or camera/vision systems. The system provides real-time data using wired or wireless communication with the operating surgeon, either located locally or remotely. The bone-mounted robot can be a stand-along device or controlled remotely using haptic feedback.

There has thus been outlined some of the features of the methods and systems of bone-mounted robotic-assisted surgery devices for hip and shoulder replacement procedures so that the detailed description herein may be better understood, and so that the present contribution to the art may be better appreciated. In this respect, it should be appreciated that the methods and systems for a bone-mounted robotic-assisted surgical system are not limited in their applications to the details of construction or the arrangements of the components outlined in the following description or illustrated in the drawings. The methods and systems for a bone-mounted robotic-assisted surgical system are capable of other aspects and of being practiced and carried out in various ways. Also, it is to be understood that the phraseology and terminology employed herein are for the description and should be regarded as limiting.

BRIEF DESCRIPTION OF THE DRAWINGS

The various features and advantages of the technology of the present disclosure will be apparent from the following description of particular embodiments of those technologies, as illustrated in the accompanying drawings. It should be noted that the drawings are not necessarily to scale; however the emphasis instead is being placed on illustrating the principles of the technological concepts. The drawings depict only typical embodiments of the present disclosure and, therefore, are not to be considered limiting in scope.

It will be apparent to one skilled in the art after review of the entirety disclosed that the steps illustrated in the figures listed above may be performed in other than the recited order, and that one or more steps illustrated in these figures may be optional.

DETAILED DESCRIPTION

Aspects of the present disclosure involve systems, methods, computer program products, manufacture process and the like for robotic-assisted surgical systems mounted to a patient's anatomy near the surgical site. To aid in the description below, a brief discussion of the anatomy of the patient's hip, hip prosthesis design, conventional instrumentation, surgical steps, implant orientation, and conventional implant alignment techniques now included. As mentioned above, the present disclosure may be applied to any region of a patient's joints, as part of the orthopedic procedure. However, for ease of understanding, the discussion herein is limited to particulars of the hip as an example of the inventions relating to the present disclosure procedure and embodiments.

Figure 1:
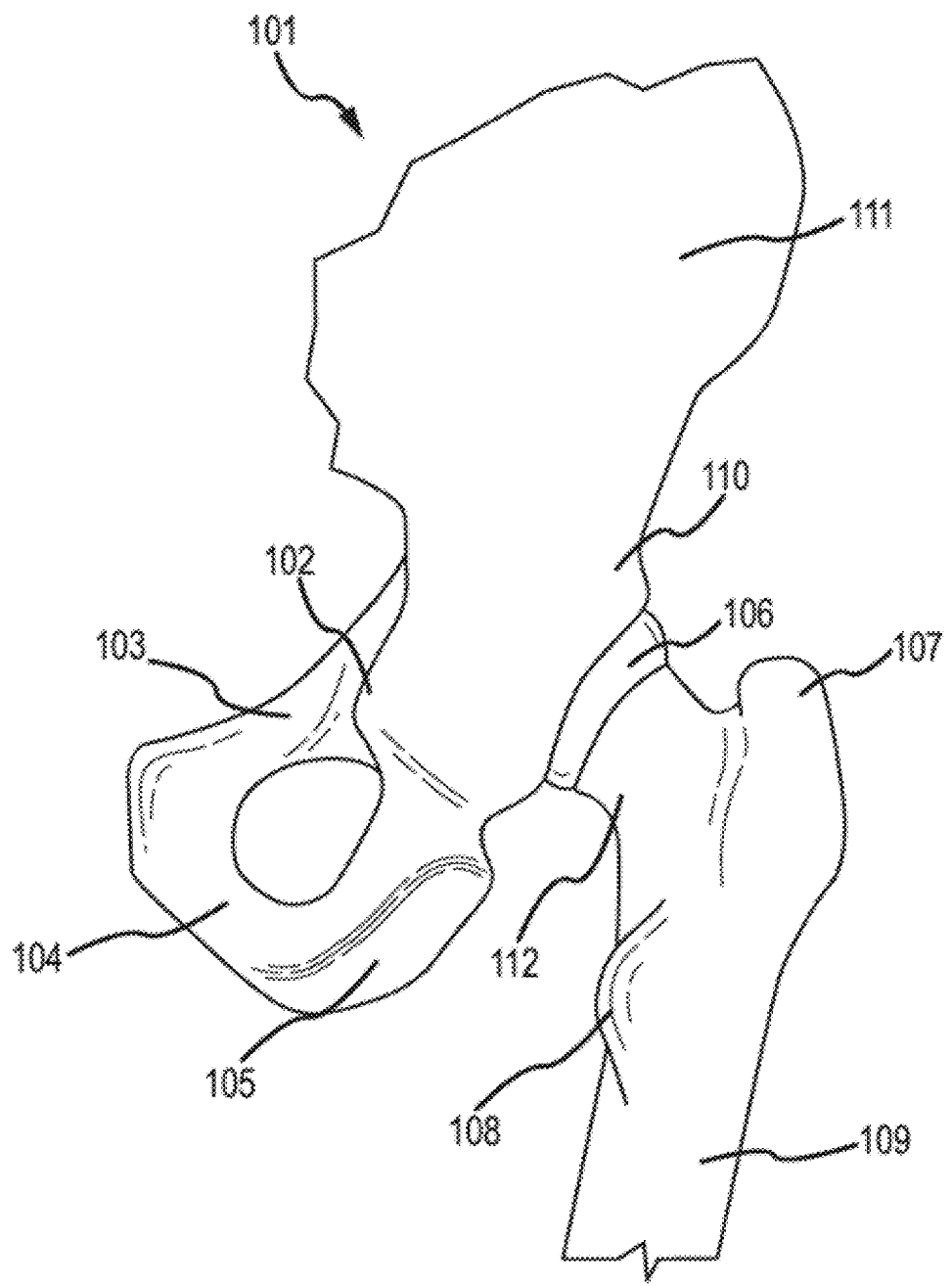
FIG. 1 is a posterior view of the human hip.
Figure 2:
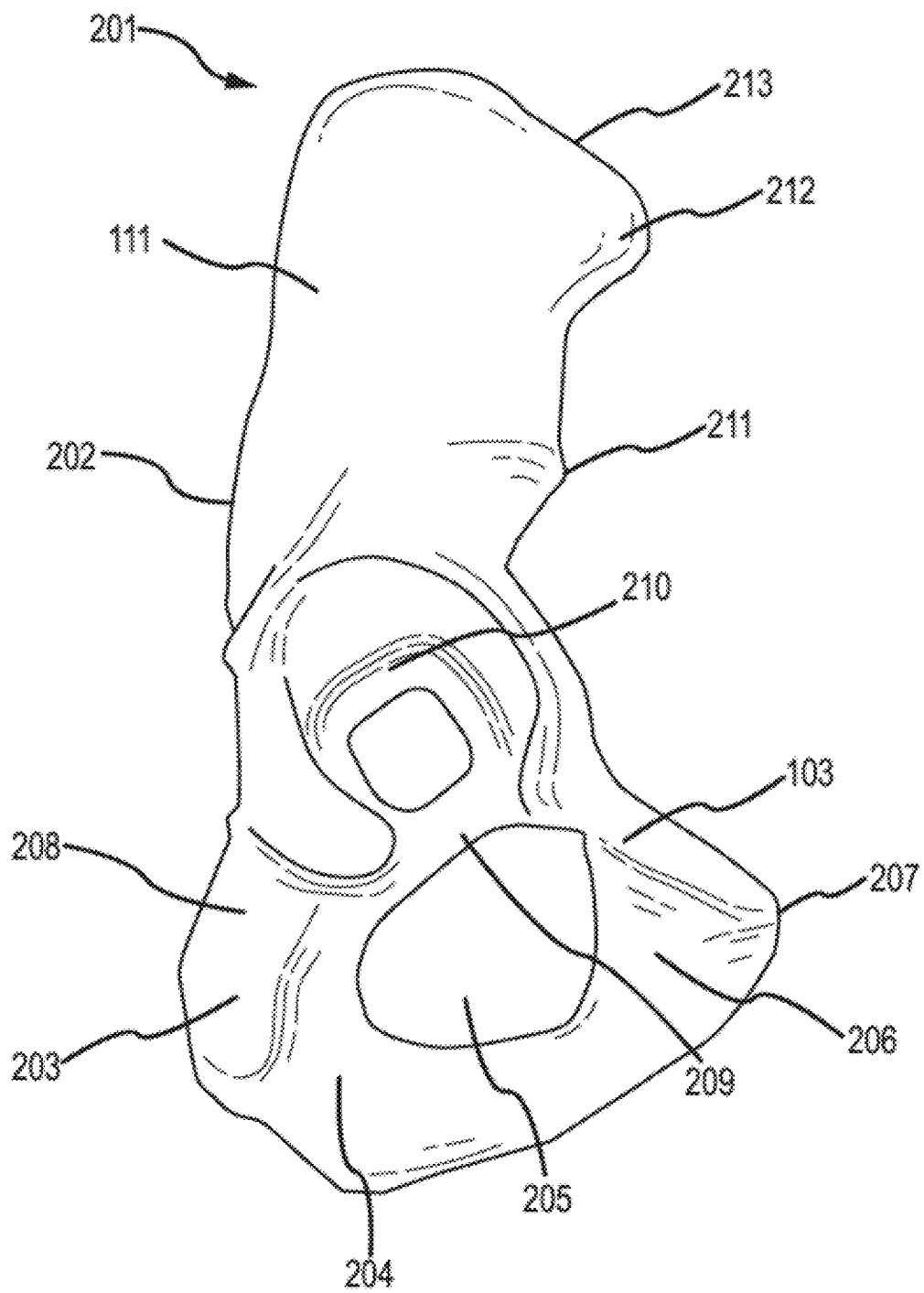
FIG. 2 is a lateral view of the human hip.

FIGS. 1 and 2 illustrate a posterior view 10 and a lateral view 201 of a human hip joint comprising a pelvis and femur connected by a ball-socket synovial joint, formed by an articulation between the femoral head 106 and acetabulum (cup) 210. Together, the hip joint forms a connection from the lower limb to the pelvic girdle and thus is designed for stability and weight-bearing, rather than a large range of motion. An ilium 111, ischium 105, and pubis 103 together form a cup-shaped socket known as the acetabulum 210 with a notch 209 located inferiorly. The ilium 111 is the widest and largest of the three part of the hip bone and is located superiorly. The body of the ilium 111 is forms the superior part of the acetabulum 210. The superior margin of the wing of the ilium is thickened, forming the iliac crest 213 extending from the anterior-superior iliac spine 212 to the posterior-superior iliac spine 202. On the anterior aspect of the ilium 111, a peak known as the anterior-inferior iliac spine 211 is present. The pubis 103 is the most anterior portion of the hip bone and comprises a pubic body 207, a superior ramus 104, and an inferior ramus 206. Together, the superior and inferior rami 206, 206 enclose part of the obturator foramen 205. The ischium 105 forms the posterior-inferior part of the hip bone. Much like the pubis 103, the ischium 105 is composed of a body, an inferior ramus 204, and a superior ramus. The inferior ischial ramus 204 combines with the inferior pubic ramus 206 to form the ischiopubic ramus 104, which encloses part of the obturator foramen 205. The posterior-inferior aspect of the ischium forms the ischial tuberosities 203 which, when sitting, support the weight of the body. Near the junction of the superior ramus and the body is the postero-medial projection bone known as the ischial spine 102. Also illustrated in FIG. 1 is the upper portion (proximal) of the femur comprising a femoral head 106, neck 112, greater trochanter 107, less trochanter 108, and shaft 109 extending to the knee joint.

Figure 3:
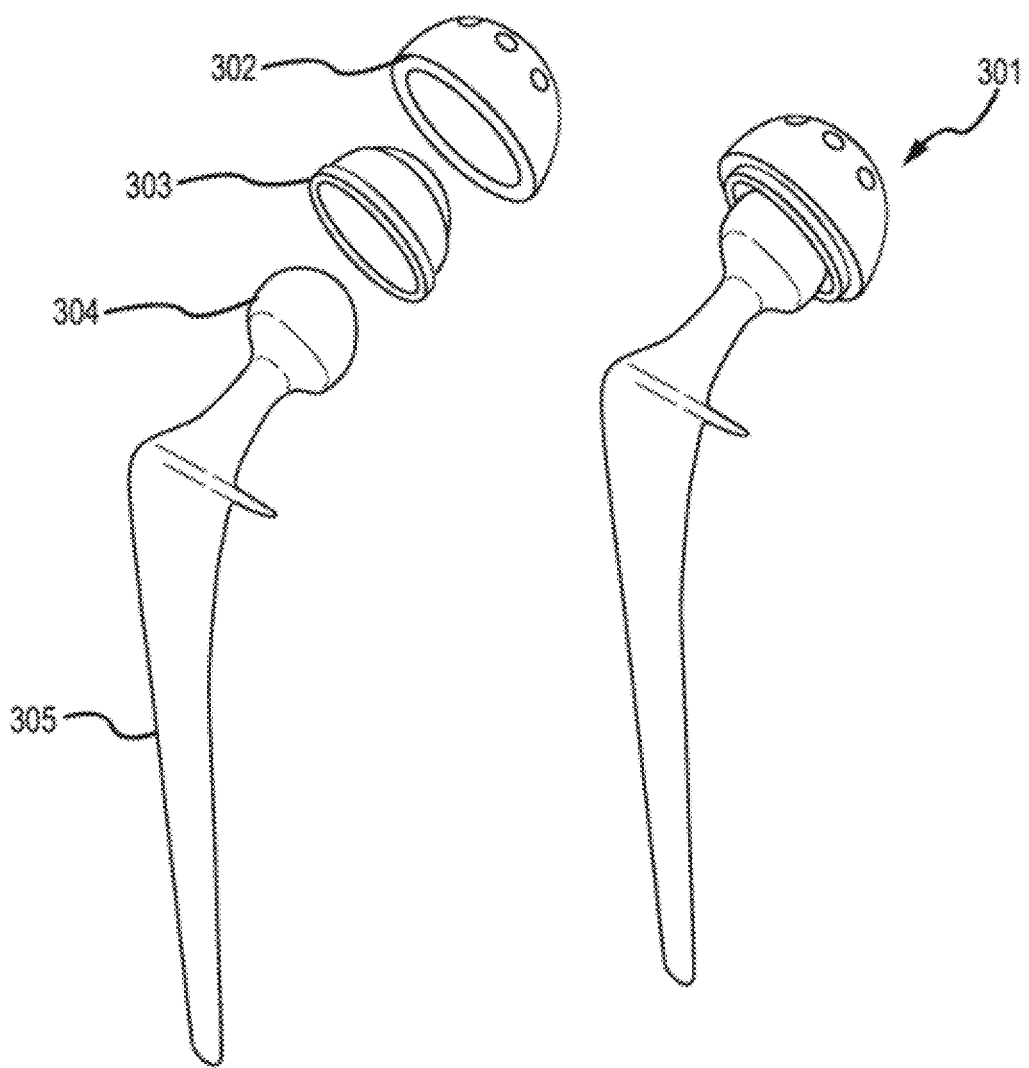
FIG. 3 is an exploded view of a hip prosthesis.

FIG. 3 illustrates a hip joint prosthesis 301 used in total hip arthroplasty, comprising an acetabular shell 302, plastic liner 303, femoral head 304, and femoral stem 305. There are various types of materials and implant sizes to accommodate different patient's hip joint. For example, hip prostheses may be made from metals, ceramics, or plastic materials, such as titanium, cobalt-chrome, stainless steel, zirconia, alumina, and polyethylene. The average formal head diameter of the natural hip is approximately 48 mm for female anatomy and 55 mm for male anatomy. To accommodate the femoral head diameter of multiple patients, most acetabulum shells 302 are sized 40 to 70 mm (referring to an outer diameter), typically increasing in size by 2 mm. Metal shells are 5 mm in thickness to prevent fatigue fracture. A shell 302 can accommodate varying thickness of the liner 303. For example, a size 50 mm shell 302 can be fitted to both a size 28 mm and size 32 mm femoral head 304 using different liner 303 thickness. A properly sized, positioned, and oriented shell 302 prevents hip dislocation and improves range of motion by balancing the soft tissues surrounding the hip joint. Other factors that contribute to a wide range of dislocation and complication incidence rates include surgical technique, component design, and surgical approach (i.e., anterior vs. posterior). One of the most common complaints of patients following a hip replacement surgery is leg length discrepancy between the operative and non-operative side.

Unlike most joint replacement surgeries where bone cement is used extensively to bond the prosthesis to the patient's bone, the modern hip implant is a press-fit (cementless) design. For example, the actual acetabular shell 302 is about 1-4 mmm smaller than the instrument of the same size, creating hoop stresses that hold the shell rigidly in place, allowing bone to grow into the rough outer shall. The acetabulum shell 302 is highly polished on the femoral head side and completely coated to allow bony ingrowth on the acetabulum side. A rough surface may be created through grit blasting using aluminum oxide particles to produce irregular surfaces at 3-8 μm depth and 50-150 μm thickness, plasma spraying using molten metal in an argon gas environment, or hydroxyapatite coating comprising osteoconductive calcium phosphate applied by plasma spray. With this in mind, it is necessary to remove all of the damaged acetabulum bone creating a continuous surface for ingrowth/on growth and a tight fit of the corresponding component of the implant 301 to prevent loosening.

Figure 4:
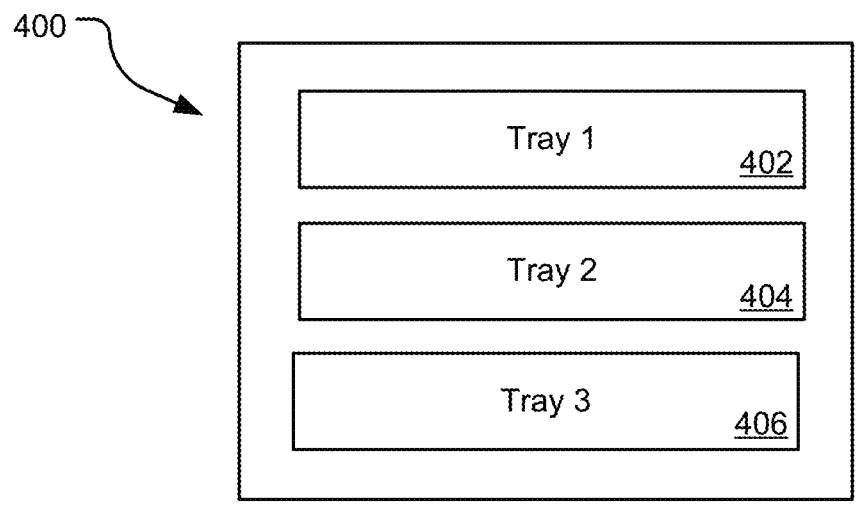
FIG. 4 is an example of a conventional instrument case used in hip replacement surgery.

Conventional instrumentation may be used for total hip replacement surgery comprising different instruments housed in trays 402-406 of a set 400, as shown in FIG. 4. Each tray 402-406 may include instruments for bone preparation and trial implants, such as the acetabular shell 302, liner 303, and femoral head 304. For example, a first tray 402 may include different acetabulum reamers, impactor handles, and other miscellaneous surgical instruments. As discussed above, the shape of the acetabulum reamers is a spherical hollow shell similar to component shell 302, except the reamers are typically larger in diameter. The surface of the reamer includes sharp cutters and apertures that extend throughout the shell. The spherical hollow reamer may be attached to a metal shaft at the center conical point using a locking device, such as vise. A second tray 404 may include a trial femoral head 304 implant (i.e., different ball sizes) and a third tray 406 may include different broach sizes for preparing an intermedullary canal for receiving a femoral stem 305. Typically, the conventional instruments are re-useable after cleaning and sterilization. Studies have shown that newer reamers cut more accurately than re-usable reamers. In outpatient surgery facilities where resources and space are limited, it may be desirable to reduce the number of instrument trays to a minimum.

Figure 5:
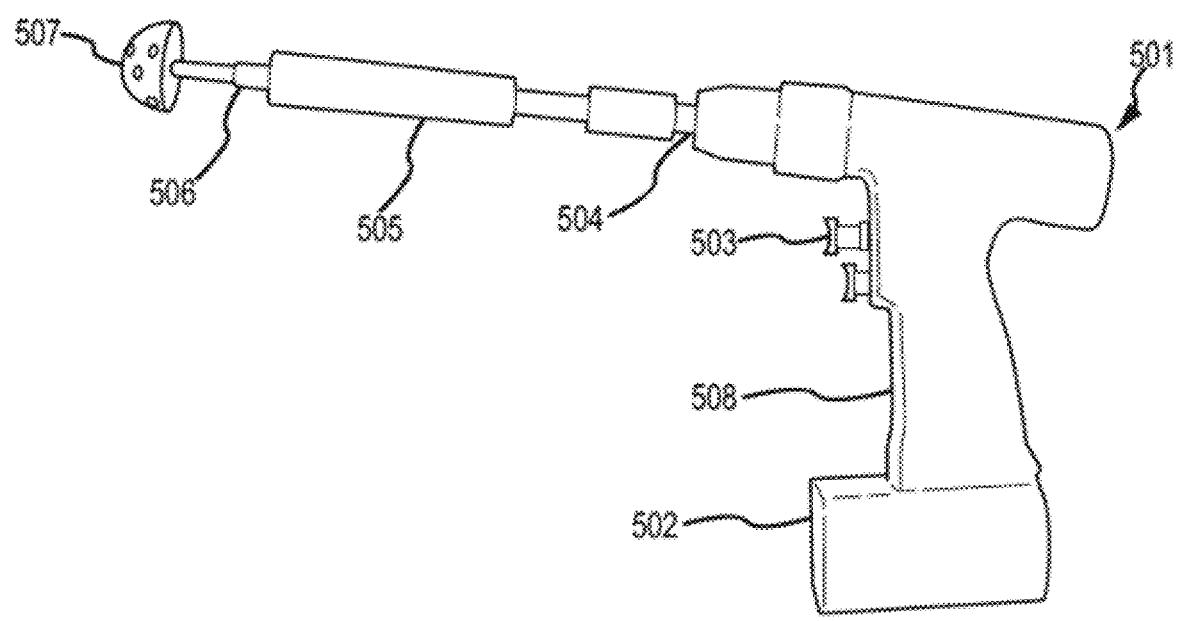
FIG. 5 is an example of an acetabular reamer assembly attached to a cordless power drill.

FIG. 5 is an isometric view of an acetabular reamer assembly attached to a cordless drill 501. The cordless drill 501 comprises a handgrip 508, battery 502, on/off/speed triggers 503, and drill chuck 504 to secure the reamer shaft 506 to the motor spindle. Housed inside the drill are electromechanical components, such as motors, gears, sensors, and electronics. In one implementation, robot controller electronics, sensor interface electronics, and communication interfaces may also or alternatively be housed inside the drill 501. The acetabular reamer may comprise a cylindrical handled or bearing sleeve 505 fitted over the cylindrical reamer shaft 506 allowing the acetabular reamer to rotate freely at high speeds while the handle is stationary. In general, the acetabular reamer 507 can be any tool, such as a ball-shaped mill, drill bit, or other cutting tool to remove damaged bone. The handle 505 allows the surgeon to use two hands during operation of the drill: one to control the triggers 503 and one to maintain the correct trajectory during reaming. As one can appreciate, this manual process may be highly inaccurate and prone to errors as the surgeon has no visual reference of the hip anatomy to maintain the desired trajectory during reaming. Also, depending on the surgical technique (i.e., minimally invasive) and approach (i.e., direct anterior, direct lateral, or posterior), it can be challenging even for the experienced orthopedic surgeon to hit the trajectory within 5 degrees of the target and within 1-2 mm of the acetabular component for each patient.

Figure 6:
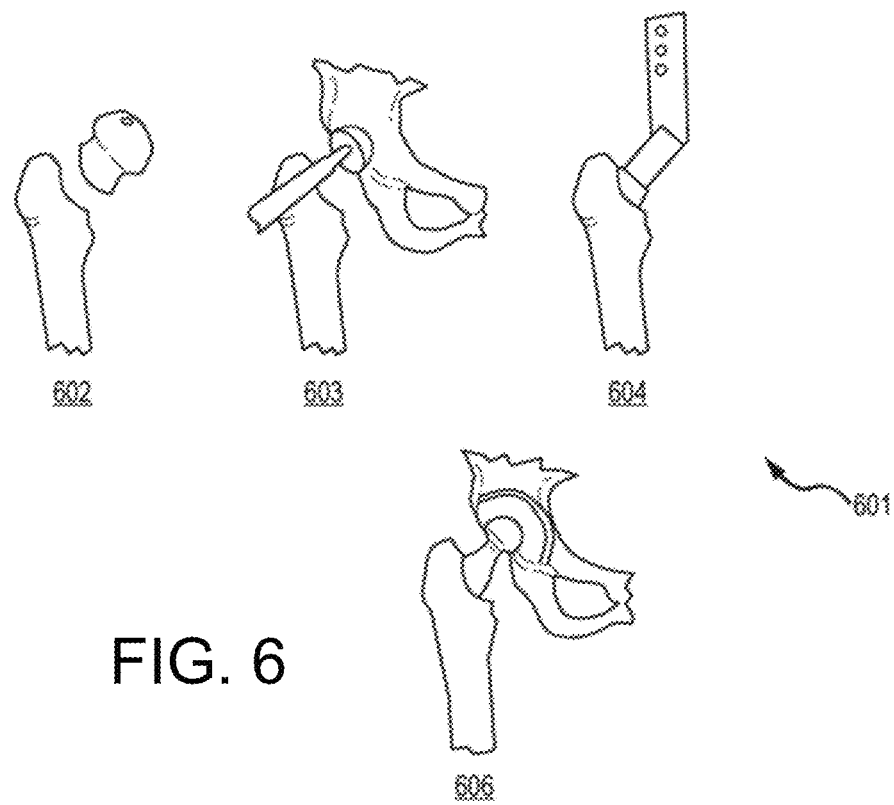
FIG. 6 is an illustration of a surgical process in total hip replacement.

FIG. 6 is a diagram illustrating the different stages 601 of a surgical procedure for a total hip replacement. The goal of the hip replacement procedure is to remove the damaged join and replace it with an artificial joint. At stage 602, the femoral head 106 portion of the femur 109, including a portion of the neck 112, is removed near the greater trochanter 107 and lesser trochanters 108. At stage 603, the acetabulum 210 is prepared via sequential reaming starting from a smaller reamer size and working up towards the target size, removing the remaining cartilage and subchondral bone to create a bed of vascular cancellous bone that encourages bone ingrowth or on-growth. As mentioned above, the surgeon may start 1-2 sizes smaller than the target size and work up to the target size reamer. For example, a final reamer size of 49 mm may be used for a size 50 mm cup. This is called "oversizing" the implant to increase hoop-stress on the implant. The reason behind this is the hemisphere created by sequential reaming may not be a perfect circle if the surgeon moves the center-point of each ream, creating an oval shape, decreasing hoop stress. Oversizing can therefore compensate for imperfect reaming. Alternatively, poor bone quality, as seen with avascular necrosis or osteoporosis, may reduce the viscoelasticity of bone, which in turn decrease its ability to generate hoop stress, and therefore, oversizing may generate better stress. However, too much hoop stress may create a facture, to which poor bone quality is more susceptible.

At stage 604, the intramedullary femoral canal is prepared to receive the femoral stem 305 of the implant via sequential broaching/removing of subchondral and cancellous bone. Similar to the acetabulum preparation, the surgeon may start with a 1-2 size smaller tool and work up to the target size as excess broaching can cause femoral facture for patients with poor bone quality. At stage 605, the target size of the femoral stem 305 and acetabulum shell 302 is impacted into the subchondral bone of the hip joint for a press-fit using an impactor instrument as part of the instrument set 400. During this process, the orientation of the acetabulum shell can vary (i.e., desired or undesired) from the reaming orientation due to the spherical shape of the implant and imperfect reaming. Also, the position, such as the center of the acetabular component, may have changed due to sequential reaming. At stage 606, the correct liner thickness is determined during a trial fit of all of the components and the femoral head 304 is inserted into the liner 303 to form a ball-socket joint. As mentioned above, the most common complications of post hip replacement surgery are dislocation and bony impingement such that correct component orientation during the procedure is desired.

Figure 7:
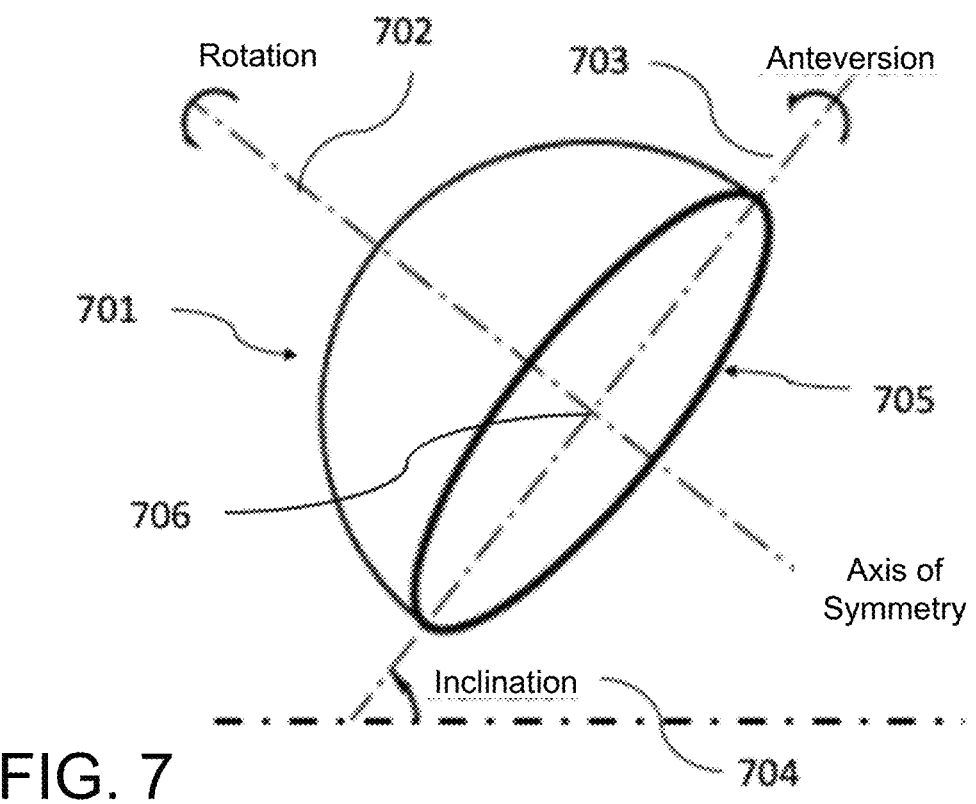
FIG. 7 is an isometric view of the acetabular cup with various orientations.

FIG. 7 is a perspective illustration of the acetabular prosthesis (shell) 302 as part of the hip prosthesis 301 indicating the various orientation angled and reference axes. As described above, the acetabular component is a spherical shell (hemisphere) shape with a center point 706, which can be intersection of three axes (anteversion, rotation, and inclination) about the face 705 of the cup. In one embodiment, the center point 706 is defined as the apex of the acetabular component along the rotational axis 702. The center of the acetabular components and the center-point of the acetabulum is not necessary the same point or location. The position of the acetabulum shell can be described using a cartesian coordinate system in terms of its center point using three-dimensional space (X, Y, and Z) while any point on the spherical shell can be described using a spherical coordinate system (r, θ, φ); where r=radius (unit of length), θ=inclination (angle in Degrees or Radians), and φ=anteversion (angled in Degrees or Radians). For near anatomic positioning, the acetabular cup placement comprises to angles; inclination 704 and anteversion 703. The "safe zone" may correspond to the native hip and implant overlap. The inclination may be about 40°±10° (abduction) and version angle is 15°±10° (anteversion). The axis of symmetry 702 represents the desired rotation or trajectory of the acetabular component. In another embodiment, the acetabular shell is a reamer oriented at the desired rotation (trajectory). In this circumstance, the axis of symmetry 702 represents the centerline of the cylindrical reamer shaft where the reamer is rotating about axis 702. Satisfactory clinical results depend on the precise orientation, as well as depth and height, of the acetabular component relative to the native hip.

Figure 8:
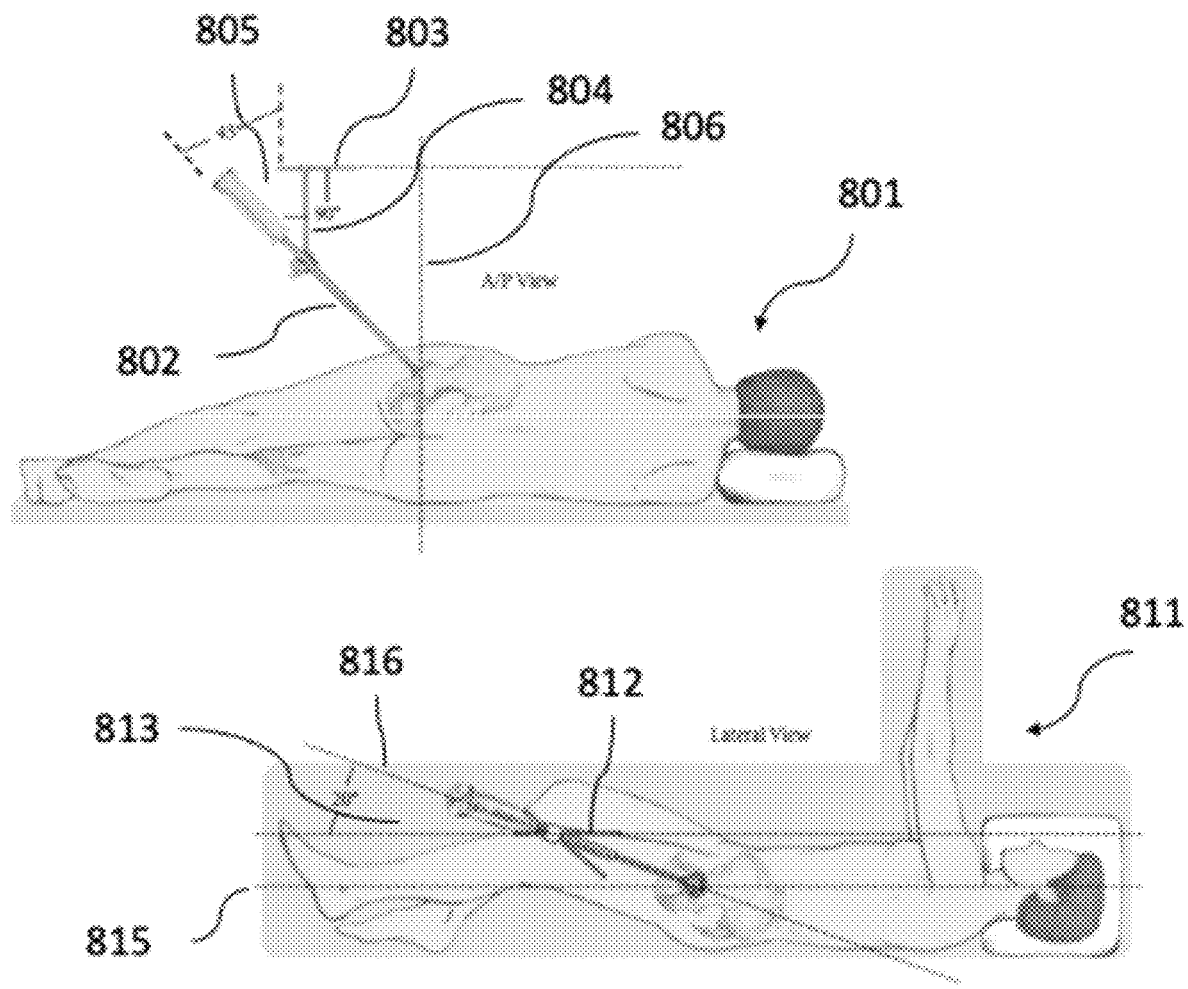
FIG. 8 is an illustration of a patient undergoing total hip replacement using conventional instruments for orienting the acetabular cup in two-planes.

As mentioned above, the final acetabular component orientation can vary after the sequential reaming. The desired component orientation can still be achieved when impacting the shell 302 into the hip socket, as shown in FIG. 8. As shown in FIG. 7, the two angles, abduction and anteversion, define the orientation of the acetabular component in spherical coordinates. The safe zone (40°±10° abduction and 15°±10° anteversion) can be achieved by aligning the cup impactor instrument at the desired angle in both anterior/posterior (A/P) 801 and lateral 811 views/planes. The abduction angle is determined in the A/P plane 801 when the patient's operative side (left) is facing up towards the ceiling while lying on its lateral side (right shoulder). Similarly, the anteversion angle is determined in the lateral plane 811 looking down at the patient's left hip while lying on its right side. Both 801 and 811 are orthogonal to each other. To achieve the desired trajectory, the impactor handle 802 is defined relative to two reference axes: inclination 816 and anteversion 803 in the A/P plane. Reference axis 806 establishes the center of the cup 706 and inclination axis 704. Line 803 is perpendicular to line 806 and parallel to the operating table. On the impactor instrument 802, a "T" shape (90°) proctor like device 804 is attached to the shaft of the impactor at approximately 45° relative to the center line 806 and parallel to the surgical table. The goal is to align the "T" shape protractor with the virtual reference axes 803 and 806, thus establishing the desired inclination angle 805 in the safe zone. Similarly, in lateral view 811, the patient is shown lying on its lateral side with the acetabulum facing upwards towards the ceiling. Two reference axes 815 and 816 are established in the lateral plane. Reference axis 815 establishes the center of the cup and parallel to the table in lateral view. Reference axis 816 is the desired trajectory of the acetabular component through the center of the cup at 20° relatives to line 815. This angle 813 represents the anteversion of the acetabular cup. The proctor like instrument 812 attached to the shaft of the impactor is set to 20° relative to the desired trajectory which is within the safe zone. As one can appreciate, achieving the desired cup orientation in two planes simultaneously is challenging even for the most experienced surgeon and highly inaccurate. Also, this alignment approach assumes that the patient's body and orientation are aligned perfectly to the surgical table in both A/P and lateral planes. For example, foam wedges or pillows are placed between the legs to create a natural position can easily cause misalignment of the acetabular component.

To assist the surgeon in performing hip replacement procedures more accurately and efficiently, surgical assisted systems, such as patient-specific instruments, computer navigation systems, and robotic surgical systems have been developed for use with image-based (such as MRI, CT, X-rays, ultrasound or other forms of imaging) or imageless. For image-based computer navigation systems, a current process includes the surgeon providing upwards of 50 or so verification points on the patient's bone as part of a registration process for mating a patient-specific instrument to the patient, which is a rather time-consuming and error-prone procedure. Another registration method may use a customized device that has features or surfaces that mates with the anatomical bony landmarks or surfaces of the patient's joint providing instantaneous registration for use with manual instruments or robots. Methods and systems for using a customized registration guide for robotic-assisted surgery are described in more detail in the U.S. patent application Ser. No. 17/091,516, entitled METHODS AND SYSTEMS FOR ROBOTIC-ASSISTED SURGERY USING CUSTOMIZED BONE REGISTRATION GUIDES, the entirety of which is incorporated by reference herein. To aid in the description below, customized femoral and acetabular devices are now included. Methods and systems for creating such customized registration guides for joint arthroplasty using two-dimensional imaging are described in more detail in the U.S. Pat. No. 10,139,807, entitled METHOD FOR CREATING A CUSTOMIZED ARTHROPLASTY RESECTION GUIDE UTILIZING TWO-DIMENSIONAL IMAGING, the entirety of which is also incorporated by reference herein. The customized device may include features, such as drill holes or saw guides, to establish the correct reference points, lines (axes), or frames. As mentioned above, the present disclosure may be applied to any region of a patient's joints, as part of the orthopedic procedure. However, for ease of understanding, the discussion herein is limited to particulars of the hip as an example of the inventions relating to the present disclosure procedure and embodiments.

As mentioned above with reference to FIG. 6, a total hip replacement procedure involves replacing the damaged joint with an artificial hip 301. During procedure 603, an oscillating saw is typically used to cut the bone along the femoral neck 112, removing the damaged head 106. To achieve the desired resection angle and location, a customized femoral resection device can be used to guide the oscillating saw in cutting bone. The methods and systems for determining the femoral resection plane using a series of 2D images are described in more detail in U.S. Pat. No. 9,925,069, entitled METHOD FOR FEMUR RESECTION ALIGNMENT APPROXIMATION IN HIP REPLACEMENT PROCEDURES, the entirety of which is incorporated by reference herein. Similarly, a customized acetabulum guide can be used to provide the desired trajectory during sequential reaming. For ease of understanding, the discussion below is limited to the customized femoral and acetabular guides for total and partial hip replacement surgery including different surgical approaches.

Figure 9:
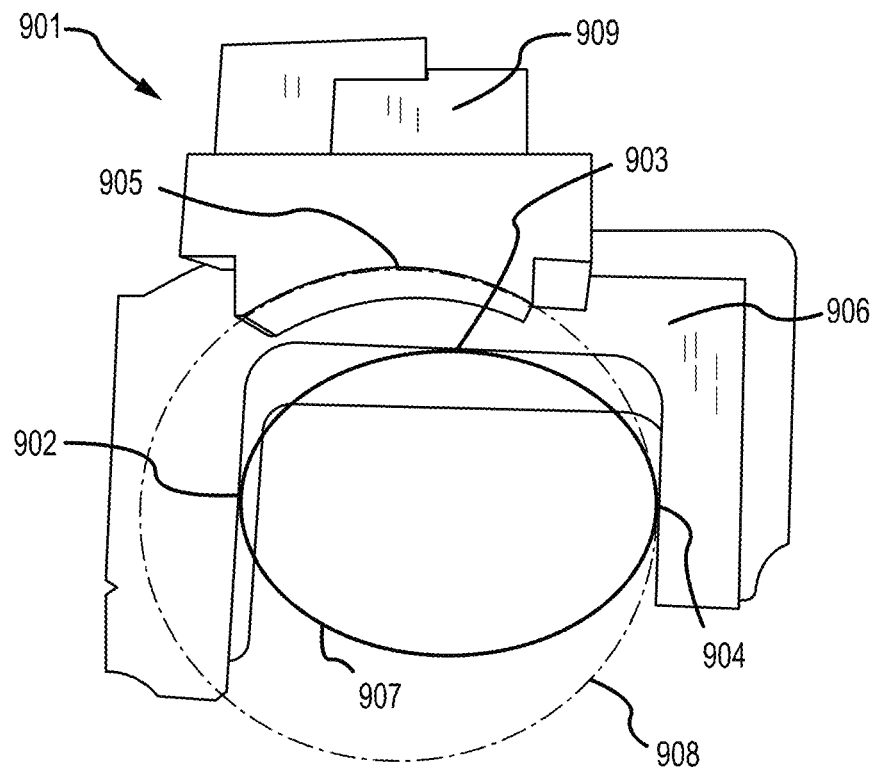
FIG. 9 is a front view of a customized femoral resection guide.

FIG. 9 is the front view 901 of one customized femoral resection guide for mating to a femoral head during a hip arthroplasty procedure. As discussed above, the hip joint consists of a spherical femoral head 106, neck 112, and shaft 109. In general, the femoral resection guide includes a first portion for mating with the femoral neck 112, which joins the femoral shaft 109 and head 106. In general, the femoral neck 112 has an elliptical cross-section. The first portion of the resection guide mates to the femoral neck 112, as illustrated by solid line 907. The spherical shape of the femoral head 106, as illustrated through dashed line 908, is also illustrated in the illustration of FIG. 9. The resection guide includes a "U"-shaped mating feature that makes contact with the elliptical-shaped femoral neck at three different contact locations or points (illustrated as points 902, 903, and 904 on the resection guide. In general, there is at least one contact point to the femoral neck 112 and the corresponding mating feature can be a point, line, ellipse, or an $n^{th}$-degree polynomial. Another mating feature 905 is circular that matches or mates with the spherical-shaped femoral head 907. This circular mating feature 905 can be described by an $n^{th}$ degree polynomial function. In general, only a portion of the mating feature 905 needs to make contact with the femoral head which is sufficient to provide stability when the guide is pressed against the bone and secured with pins using drill guide feature 909.

Figure 10:
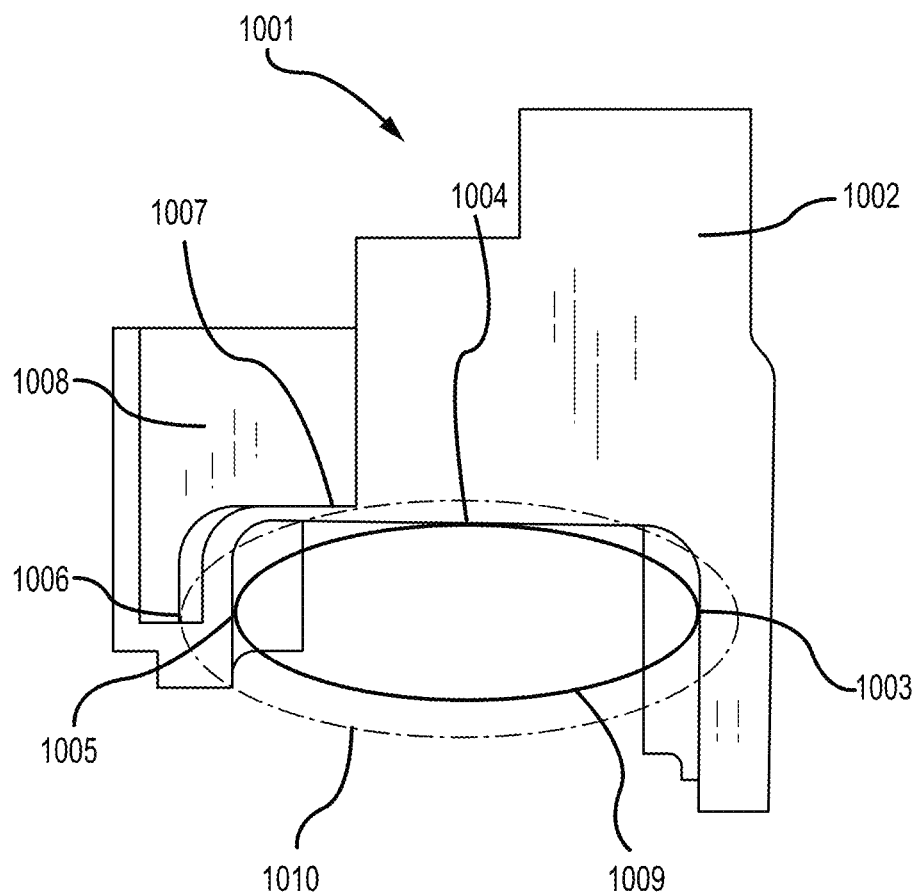
FIG. 10 is back view of a customized femoral resection guide.

As shown in the back view 1001 of the customized femoral resection guide in FIG. 10, different mating features and a saw guide 1002 may be included in the guide. Similar to the front view 901, the back of the customized guide has a "U"-shaped feature making contact with the elliptical-shaped femoral neck 1009 at three different locations 1003, 1004, and 1005. In general, the cross-section of the femoral neck 112 near the head is narrow and gradually becomes wider towards the greater and lesser trochanters such that the "U"-shaped feature may similarly taper to follow the tapering of the neck. The saw guide 1002, which may define a resection plane used during the procedure, is also a "U"-shaped feature. However, the wall of the feature has been extended proximally. The guide may include another mating feature at the back is forms an L"-shaped feature 1008 making contact with the base of the elliptical femoral neck 1010 at two different locations 1006 and 1007. In one embodiment, the "L"-shaped mating feature 1008 is making contact with the greater or lesser trochanters. In general, the "U" or "L" shaped mating feature can make contact with any part of the neck, trochanters, or shaft that has an elliptical cross-section feature.

Figure 11:
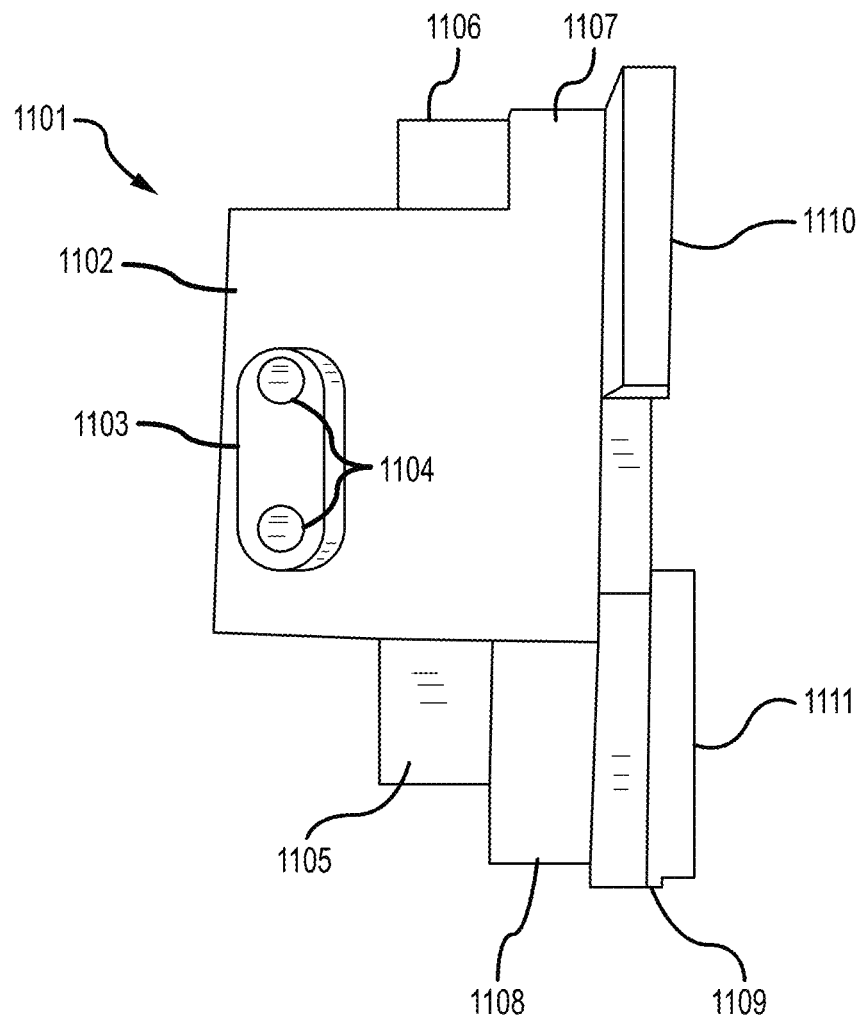
FIG. 11 is top view of a customized femoral resection guide.

FIG. 11 is the top view 1101 of the customized femoral resection guide showing the outer features of the guide. The customized guide of this view 1101 comprises a rectangular body 1102 that extends from a portion of the femoral head to approximately the greater or lesser trochanter. Starting from the femoral head end, the body 1102 has a raised elliptical feature 1103 that contains two holes 1104, approximately 3.2 mm apart in some instances. The purpose of the raised elliptical feature 1103 is to guide one or more drill bits when securing the guide 1101 to the femoral head/neck. As discussed above, the purpose of the circular mating feature underneath 1103 is to provide mating stability and support while drilling. On the other end of the body 1102 towards the base of the femoral neck is a saw guide 1110 connected at the end of the body 1102. On the opposite side of the saw guide is the "L"-shaped feature 1111 also connected at the end of the body 1102. Depending on the location of the resection plane, the "L"-the shaped feature 1111 can extend well beyond the saw guide feature 1110. Next, the "U"-shaped mating features 1105-1106 in view 901 and 1107-1108 in view 1001 are connected to the body perpendicularly and parallel to the saw guide 1110 and "L"-shaped feature 1111 and located between the drill guide and saw guide features. In general, the order of the mating features can vary depending on the shape of the bone and resection plane. Also, the end of the saw guide 1110 and "L"-shaped 1111 features can also make contact with the bone using any part of the guide including points, lines, or planes.

Figure 12:
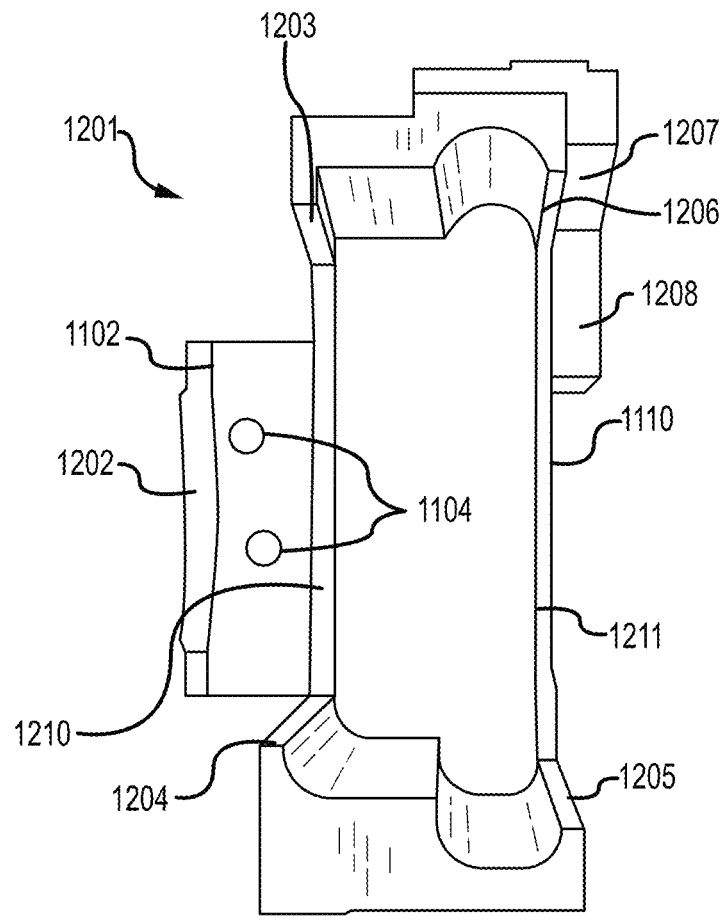
FIG. 12 is bottom view of a customized femoral resection guide.

FIG. 12 is the bottom view 1201 of the customized femoral resection guide showing the different mating features, locations, and the various contact points with the bone. In particular, drill holes 1104 may be located between the circular contact feature 1202 and the first "U"-shaped feature 1203, 1204, and 1210. In general, the location of the drill holes 1104 can be anywhere on the body 1102 along with the femoral head/neck. Similarly, for the saw guide 1110, the location and orientation may depend on the desired resection plane. As discussed above, the mating features are designed to make contact with the bony landmarks of the femoral head 106, neck 112, and other bony landmarks, such as the greater and lesser trochanter 107, 108. As such, the thickness of the contact features may vary from about 1 to 6 mm depending on the slice thickness of the imaging scan and the shape of the bone. For example, the circular contact feature 1202 may be about 3 mm, "U"-shaped contact features 1203, 1204, 120, 1206, 1211, and 1205 may be about 1 mm, and the "L"-shaped contact feature 1111 may be about 6 mm in thickness. Also, the distance between contact points 1203-1204 and 1205-1206 may vary depending on the cross-sectional radius of the femoral neck based on the orientation of the guide for a particular surgical approach.

The mating features and contact points described above are not limited to the shape, location, or number. For example, an octagon shape feature can be used as a mating feature to provide stability for the customized femoral resection guide. In one embodiment, each mating feature is modular and connected to the body 1102 individually or in groups to construct the guide. In another embodiment, the "U"-shape contact features may be adjustable and configured to a desired width matching the largest cross-sectional radius of the femoral neck. One of the advantages of using a modular or adjustable design is that it can be configured right before surgery without any delay in the production process. Also, it is not necessary to have each of the mating, drilling, and saw guide features described above as part of the customized femoral guide to fit securely on the bone. In general, these features can be optimized, added, or removed for each patient undergoing a particular type of hip procedure using a particular type of implant, such as femoral head resurfacing, mini-stem, or long stem and surgical approach. More details will be described below for the different surgical approaches and hip replacement procedures.

Figure 13A:
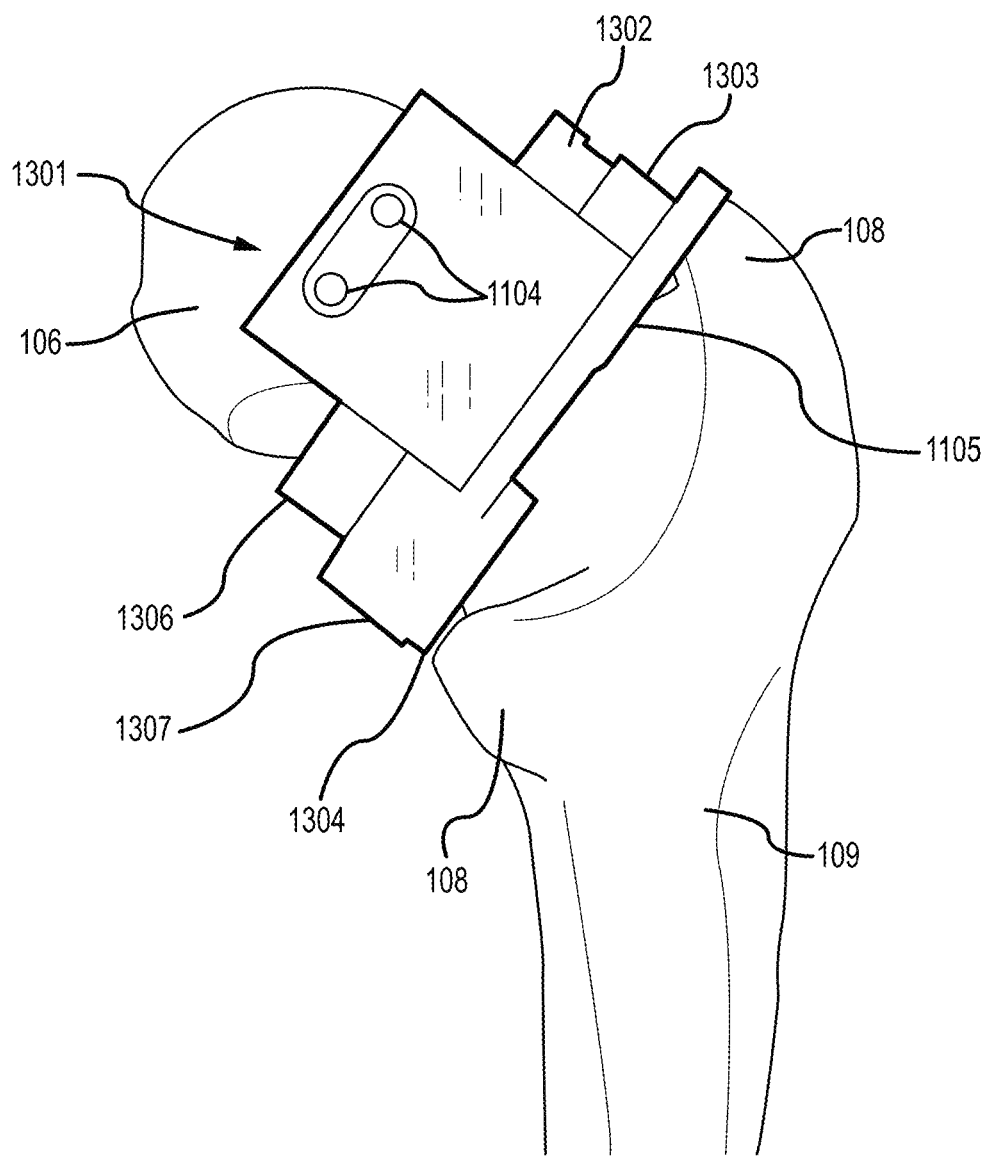
FIG. 13A is a top view of a customized femoral resection guide for the posterior approach.

FIG. 13A is an illustration of a customized femoral resection guide 1301 for a posterior surgical approach using a standard femoral stem 305 implant. Underneath the drill holes 1104 of the guide, a circular contact feature mates with the spherical femoral head 106, as described above. The first "U"-shaped mating feature is located beneath the head with contact features 1302 mating with the superior part of the neck and 1306 mating with the inferior part of the neck. A third contact point 903 (not visible in the illustration) mates with the same femoral cross-section as 1302 and 1306. The orientation of the cross-sectional slice may be determined from the orientation of the imaging scan of the patient's hip and can be reformatted to any desired orientation. In general, the imaging 2D slices are aligned perpendicular to the central axis of the femoral head, neck, femoral shaft 109, or the implant. The second "U"-shaped feature makes contact at the base of the neck near the greater 107 and lesser 108 trochanters with contact feature 1303 at the superior part of the neck and 1307 at the inferior part of the neck. Similarly, the third contact feature 1004 (not visible) makes contact with the same cross-sectional bone as 1303 and 1307. The third "L"-shaped mating feature 1304 is located at the base of the neck near the lesser trochanter 108, making contact with the cross-section of the bone superiorly and posteriorly. The saw guide feature 1105 may be located at the base of the neck near the greater trochanter 107. In some instances, the resection plane can be the same or different than the cross-section of the femoral neck (2D imaging slice orientation).

Figure 13B:
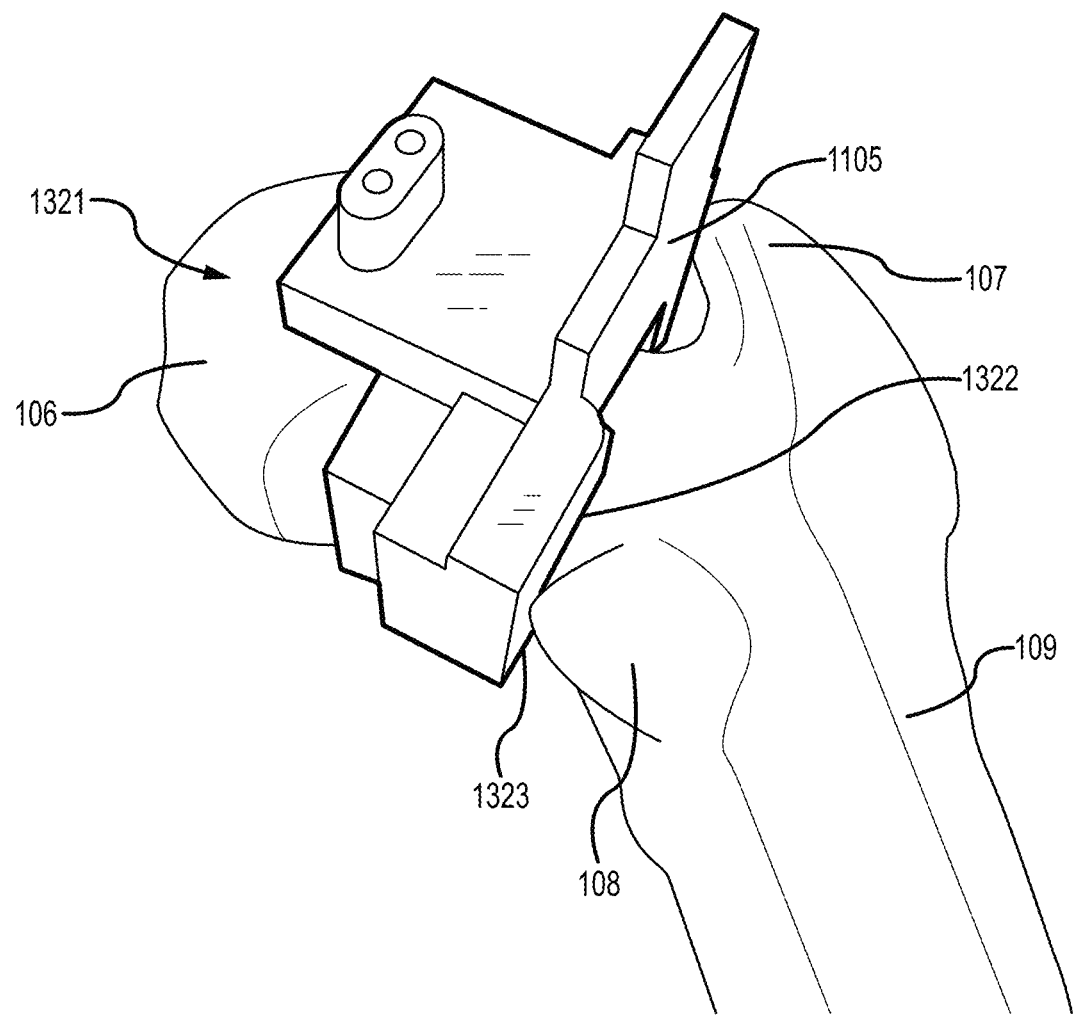
FIG. 13B is an oblique rear view of a customized femoral resection guide for the posterior approach.

FIG. 13B is an oblique view 1321 of the customized femoral resection guide 1301 showing the saw guide 1105 and "L"-shaped contact feature 1304 for the posterior surgical approach. In this view, the saw guide 1105 is illustrated with a raised wall to provide additional guidance and stability for use with a flat saw blade to achieve an accurate resection. In one example, the flat saw blade may be about 1.27 mm in thickness. The saw guide 1105 can, in some instances, be open or slotted depending on the surgeon's preference. The "L"-shaped feature 1304 is illustrated making contact with the base of the femoral neck at three locations: posterior 1322, inferior 1323, and lesser trochanter 108. In one embodiment, the "L"-shape feature 1304 is making contact with the lesser trochanter 108 at one or more locations (i.e., posteriorly and inferiorly). In general, however, the customized femoral resection guide 1301 can extend from the femoral head 106 to the femoral shaft 109, including the trochanters 107 and 108.

Figure 13C:
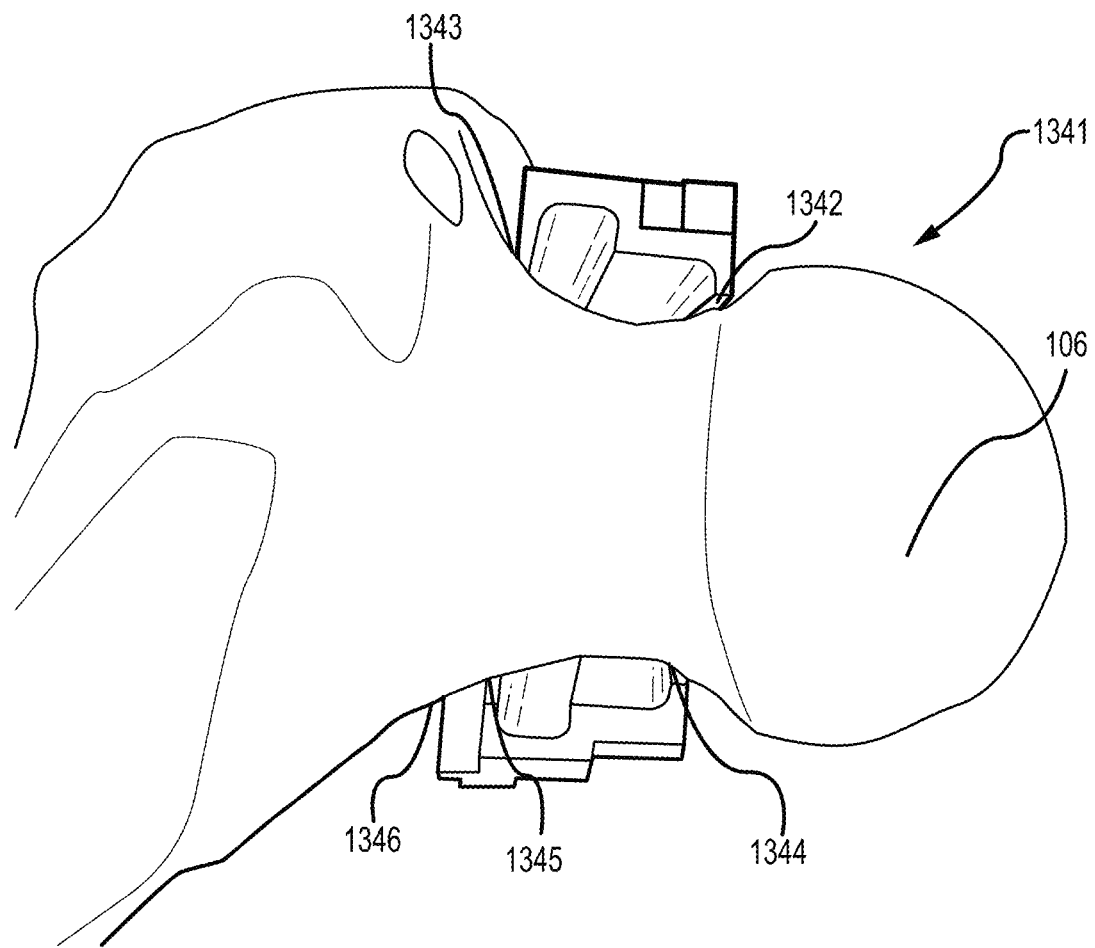
FIG. 13C is a bottom view of a customized femoral resection guide for the posterior approach.

FIG. 13C is an anterior view 1341 of the posterior customized femoral resection guide 1301 showing the inferior and superior contact points of the "U"-shaped and "L"-shaped mating features 1304. The first "U"-shaped mating feature is located at the base of the head 106 with contact points 1342 at the superior apex and 1344 at the inferior apex (major axis of the femoral neck cross-section). The second "U"-shape is located near the base of the neck with contact points 1343 at the superior apex and 1345 at the inferior apex. Finally, the "L"-shaped feature 1304 is located near the lesser trochanter with contact point 1346 located at the inferior apex of the femoral neck cross-section. In general, the mating features can make contact at any location along with the elliptical shape of the femoral neck and spherical head 106.

Figure 13D:
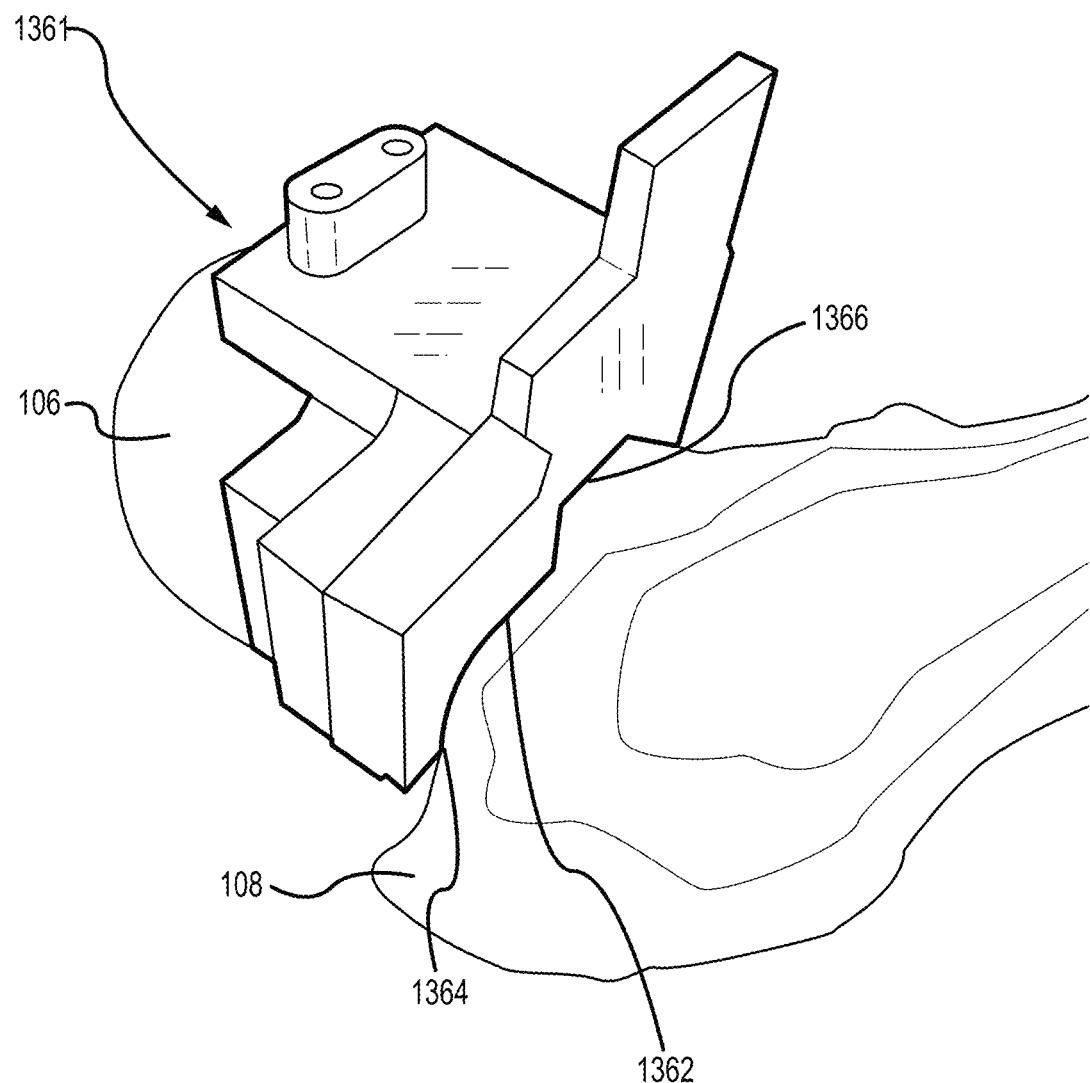
FIG. 13D is an oblique top view of a customized femoral resection guide for the posterior approach.

FIG. 13D is an oblique view 1361 of the customized femoral resection guide 1301 for an anterior surgical approach. The mating features, drill guide, and saw guide are the same as discussed above, except the customized guide in this example is placed on the anterior side of the femoral neck. In this orientation, the spherical mating feature 1202 contacts with the femoral head 106. Similarly, the "U"-shaped mating features contact the femoral neck just below the head and at the base. The "L"-shaped feature contacts superiorly at 1364 and anteriorly at 1362. Note the saw guide 1110 and "L"-shaped feature 1111 may be located on the opposite or same sides. In one embodiment, the saw guide is an additional "U"-shaped mating feature contacting the femoral neck cross-section at least one or more contact points 1366. In general, any of the mating features can also have a drill or saw guide features while contacting the bone surface.

Figure 13E:
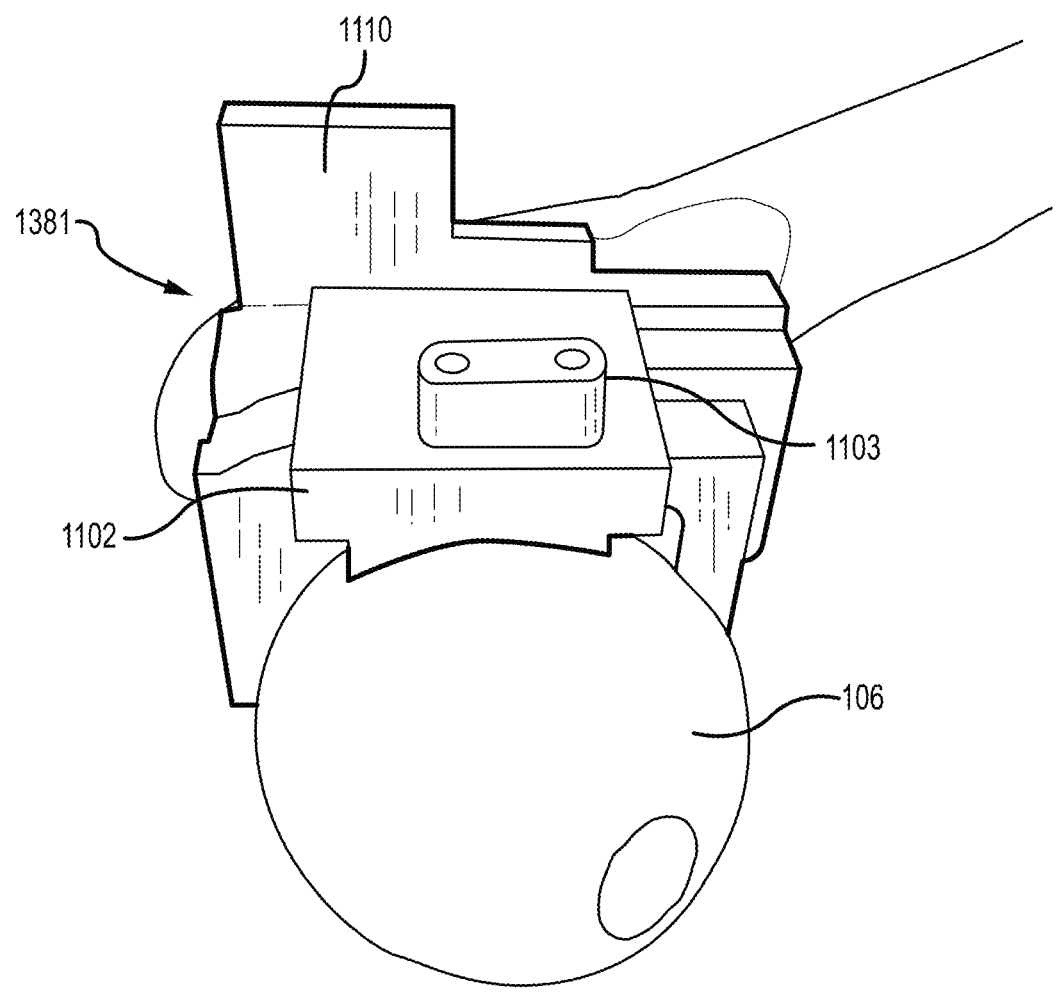
FIG. 13E is an oblique front view of a customized femoral resection guide for the posterior approach.

FIG. 13E is a perspective front view 1381 of the customized femoral resection guide 1301 showing the approximate dimensions and shapes of the various features. In one particular implementation, the rectangular body portion 1102 of the guide may be approximately 30 mm long, 25 mm wide, and 8 mm tall. The overall dimensions may be slightly larger when the mating features, drill guide 1103, and saw guide wall 1110 are added to the body 1102. The outer shape of the customized guide may comprise mostly rectangular features and elliptical features. In some implementations, the guide 1301 may include such shapes as it is faster for a CNC machining to move in a straight line than curvilinear using a 3 or 4-axis milling machine. For 3D printing, there is generally no limitation in terms of the shapes that can be used as mating features or the outer shape of the guides.

Figure 14A:
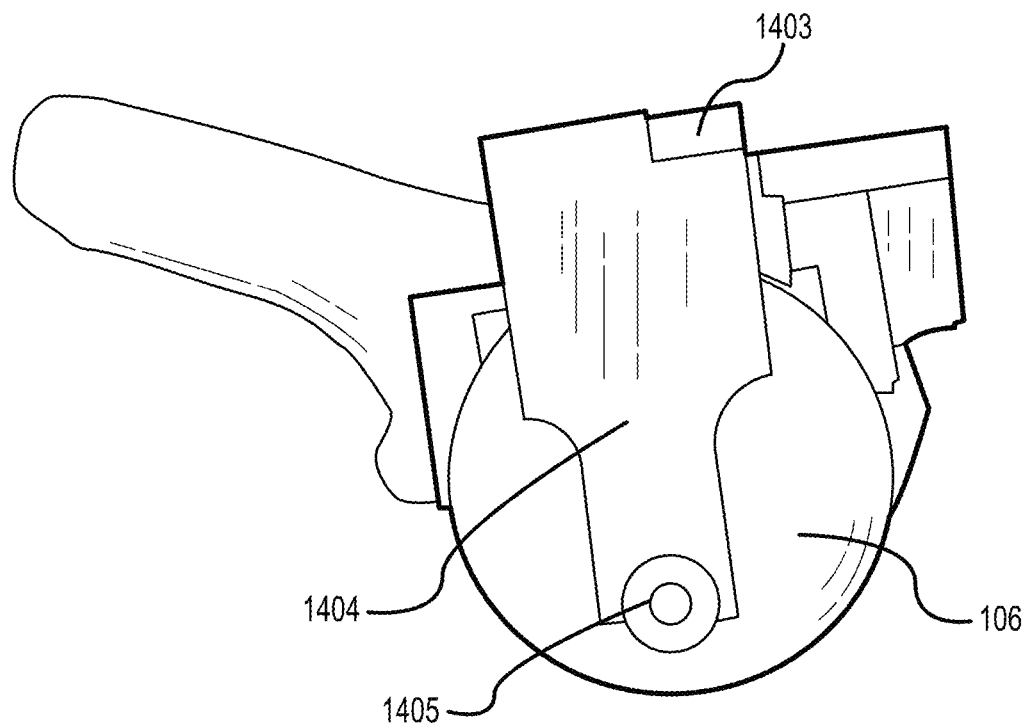
FIGS. 14A and 14B are coronal and sagittal views of a customized femoral head resurfacing guide for the anterior approach.
Figure 14B:
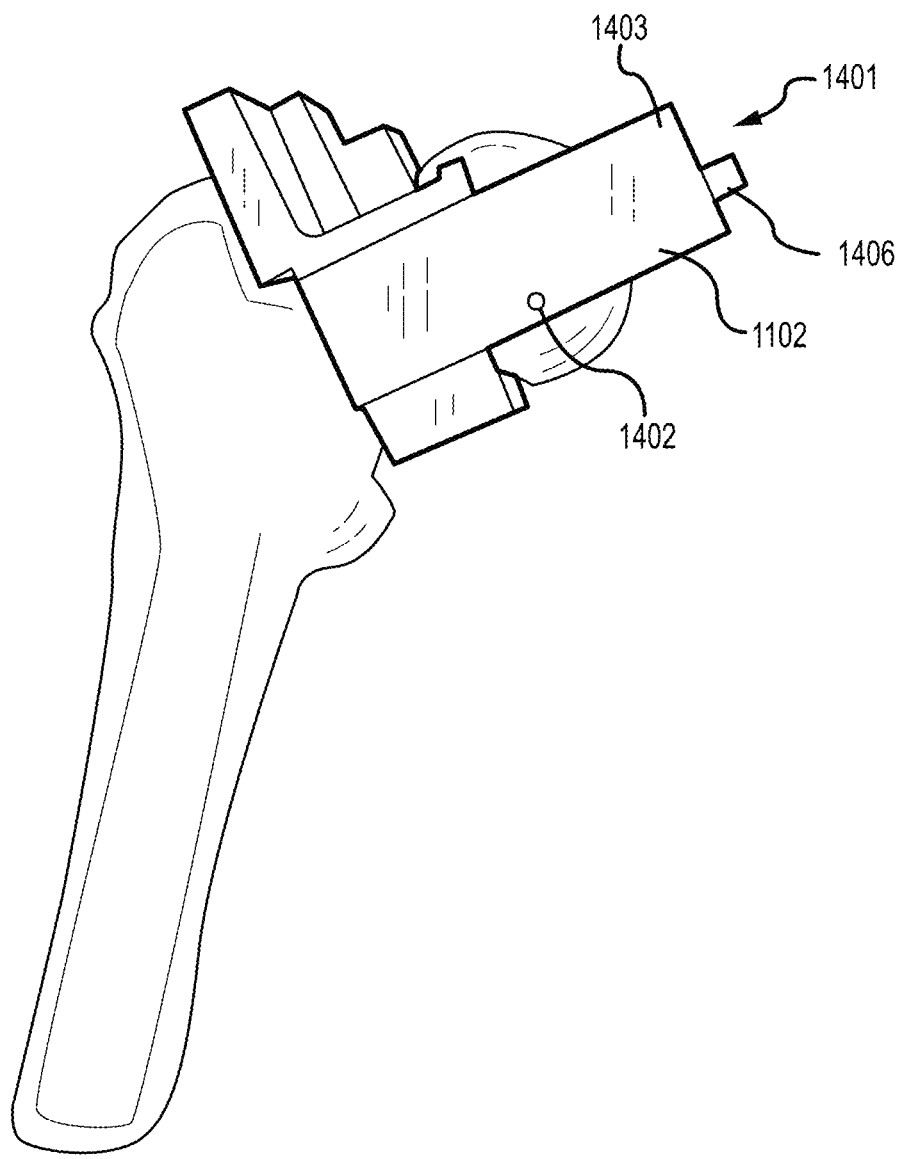

FIG. 14A is a coronal and FIG. 14B is a sagittal view of a customized femoral head resurfacing guide 1401 for the anterior surgical approach. As shown in both views, the customized surgical guide may be similar to above except the saw guide 1110 may not be required for femoral resurfacing since the head is intact. Also, the drill guide 1103 and drill holes 1104 are relocated to a different location as not to interfere with the resurfacing procedure. New locations 1402 and 1403 are slightly off-axis from the center of the femoral head/neck axis in the coronal plane. Also, the drill hole 1403 may be angled (such as 45°) towards the femoral head since the body 1102 has been extended in length beyond the end of the femoral head to accommodate the perpendicular arm 1404. Protruding from the end of the arm 1404 may be a drill guide 1406 with a hole. In one implementation, the drill hole 1406 may be about 3.2 mm in diameter 1405, as shown in FIG. 14A. During a procedure, a pin may be drilled into the femoral head and neck, guiding the hollow reamer when removing the damaged bone of the femoral head 106 at the desired trajectory. In general, however, the customized femoral resurfacing guide can support any surgical approach.

Figure 15A:
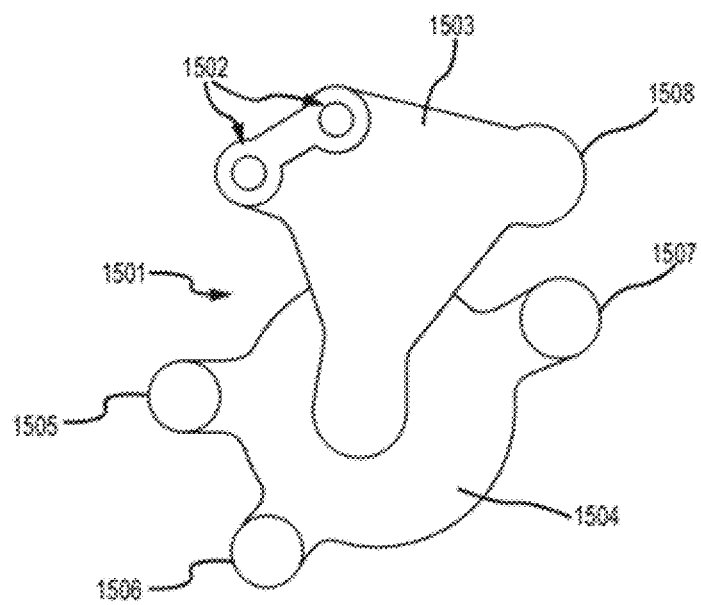
FIG. 15A is a top view of the customized acetabular registration device.
Figure 15B:
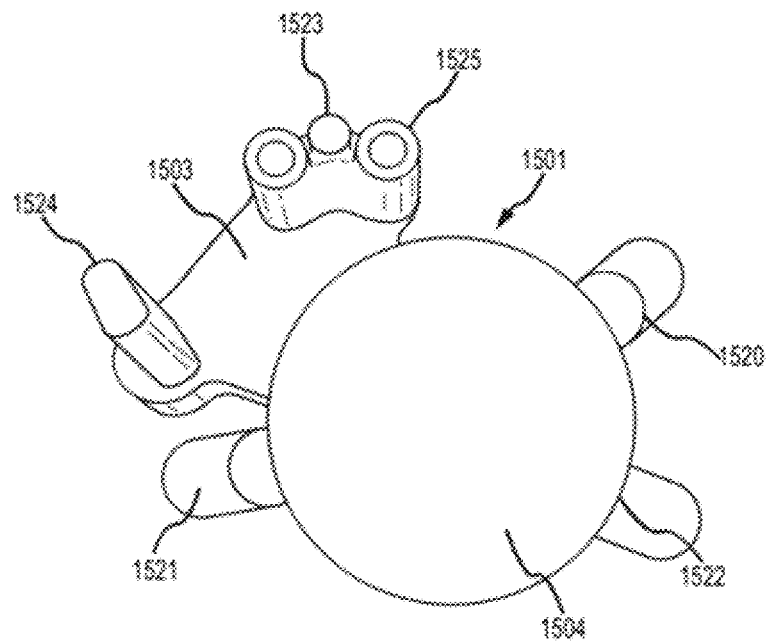
FIG. 15B is a bottom view of the customized acetabular registration device.
Figure 15C:
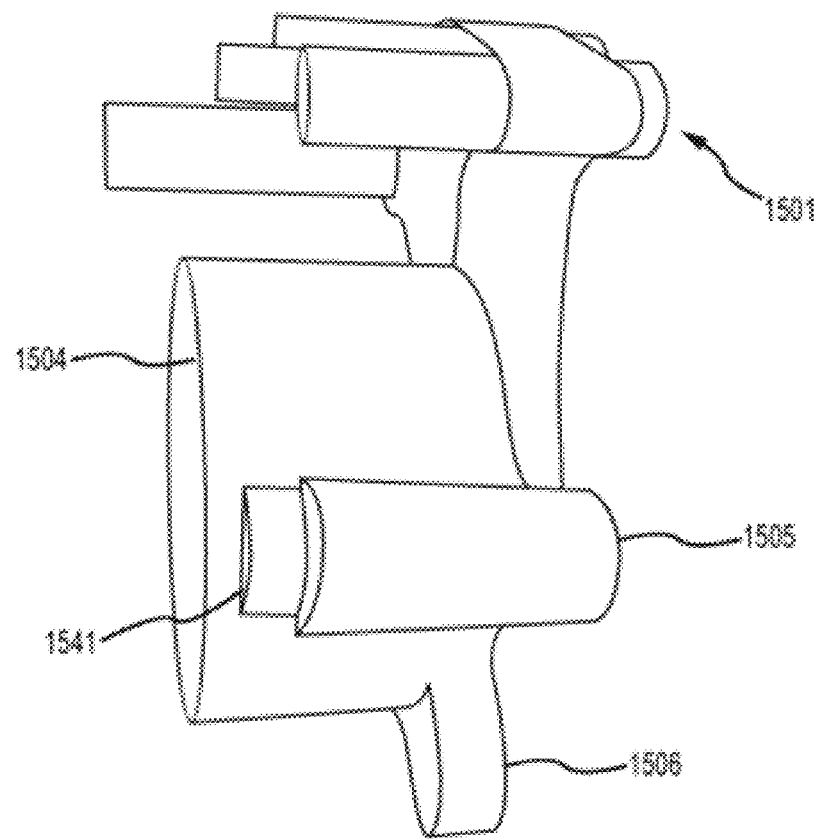
FIG. 15C is a side view of the customized acetabular registration device.

FIGS. 15A-C are the top, bottom, and side illustrations, respectively, of the custom registration acetabulum guide 1501 used in a hip replacement surgery. As shown in FIG. 15A (top view), the customized acetabulum registration guide 1501 comprises a circular body 1504 and three cylindrical mating shapes (arms) 1505, 1506, and 1507 extending outward from the edge of the body at various angles. In general, at least one or more cylindrical contact feature extending outward are connected to the main body 1504. A second body 1503, generally triangle-shaped, may be attached to the top of the body 1504 near the center with the base extending superiorly. The guide 1501 may include two drill hole features 1502 at the base near the left side of the triangular body 1503. On the right side of the base is another cylindrical feature (arm) 1508 extending outward. The triangular body 1503 can also be considered as a handle for the circular body 1502. As shown in FIG. 15B (bottom view), the arms 1505, 1506, and 1507 underneath the circular body 1504 are illustrated as including semi-circle contact features 1520 and 1521 that mate with the cavity of the acetabulum. In general, the semi-circle contact features are the same shape as the arms 1505 and 1507 but may be shorter in length, creating a step-like feature 1541 (as shown in FIG. 15C). The height of the step can be from 0 mm to the height of the main body 1 arm. When the height of the semi-circle is 0 mm, the circular feature of the main body 1522 contacts the acetabulum bone when mated. In general, the shape of the acetabulum is not a perfect circle, therefore the semi-circles provide lateral stability by creating a step feature with the arm.

Continuing with FIG. 15B, the second body 1503 comprises drill guides 1525 that are perpendicular and extruding outward. Attached between the drill guides 1525, is a cylindrical feature 1523 that mates with the ilium, superior to the acetabulum. The purpose of this contact feature 1523 is to provide stability to the guide 1501 while securing/drilling the pins to the bone, as the drill guides are generally not contacting the bone. In one embodiment, the drill guides 1525 contact the bone at one or more locations eliminating the cylindrical contact feature 1523. On the opposite side of the drill guides, 1525 is elliptical mating feature 1524 extruding perpendicularly from the body 1503. This mating feature 1524 makes contact at the junction of the pubis 207 and ilium 111 near the anterior inferior iliac spine 211 extending past the bone edge posteriorly. In FIG. 15C, a side view of the guide 1501 showing arm 1505 extending outward and downward from the body 1504 is shown. In one embodiment, the arm 1505 may be about 25 mm thick. At the bottom of the arm 1505 is the step-like (overlapping cylinder and semi-circle) feature 1541. Compare with arm 1506, this feature contacts the acetabular rim only. In general, the arms can extend outward and downward, similar to the legs of a tripod. Depending on the orientation of the guide 1501, each leg of the tripod contacts the rim at different heights from the top of the circular body 1504. When the guide 1501 is placed on the acetabulum, light pressure is applied while turning the guide 1501, using the handle, counterclockwise until it stops. The elliptical mating feature 1524 acts as a stopper preventing the guide from rotating. In general, guide 1501 may utilize seven or more contact points providing a secure lock onto the bone when mated.

Figure 16:
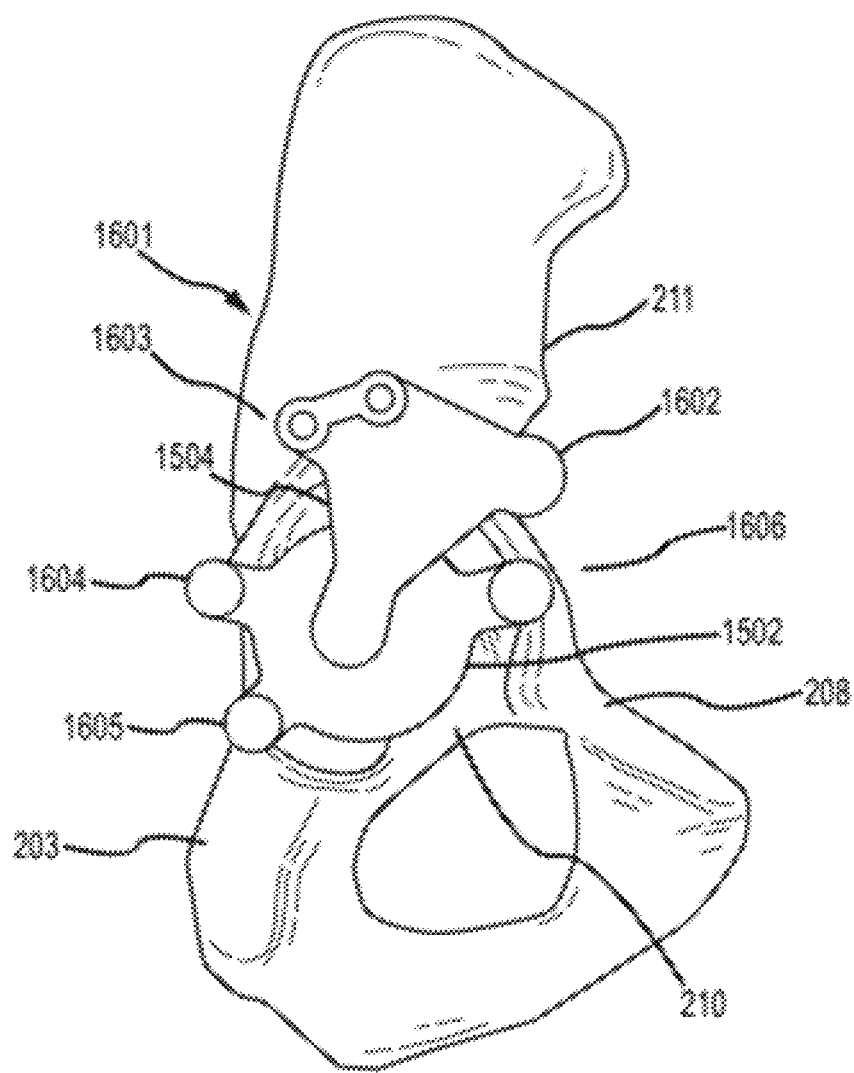
FIG. 16 is an illustration showing the customized acetabular registration device mating to the patient's bone.

FIG. 16 is a sagittal view of a pelvis 1601 showing guide 1501 mounted on the acetabulum 210. As mentioned above, the elliptical mating feature 1524, when mated, contacts the edge of the bone at the junction of the ilium and pubis 1602. The other cylindrical feature 1523 contacts the ilium bone surface at location 1603. These two contact points may prevent the guide 1501 from rotating when mated. The circular body 1504 is shown as slightly smaller in circumference to fit within the cavity of the acetabulum 210. One of the arms 1507 extending from the edge of the circular body 1502 contacts the acetabulum rim at a location part of the pubic body 208. The second arm 1505 also extending from the edge of the circular body 1502 is resting on the acetabulum rim at a location part of the ischial body. Finally, arm 1506 extending from the edge of the circular body 1504 contacts the rim of the acetabulum at a location near the ischium 203 below arm 1604. Together, the three arms form a stable platform similar to a tripod. To provide a stable guide in 3 planes, seven or more mating features may contact the ilium, pubis, and ischium forming the acetabulum.

Figure 17:
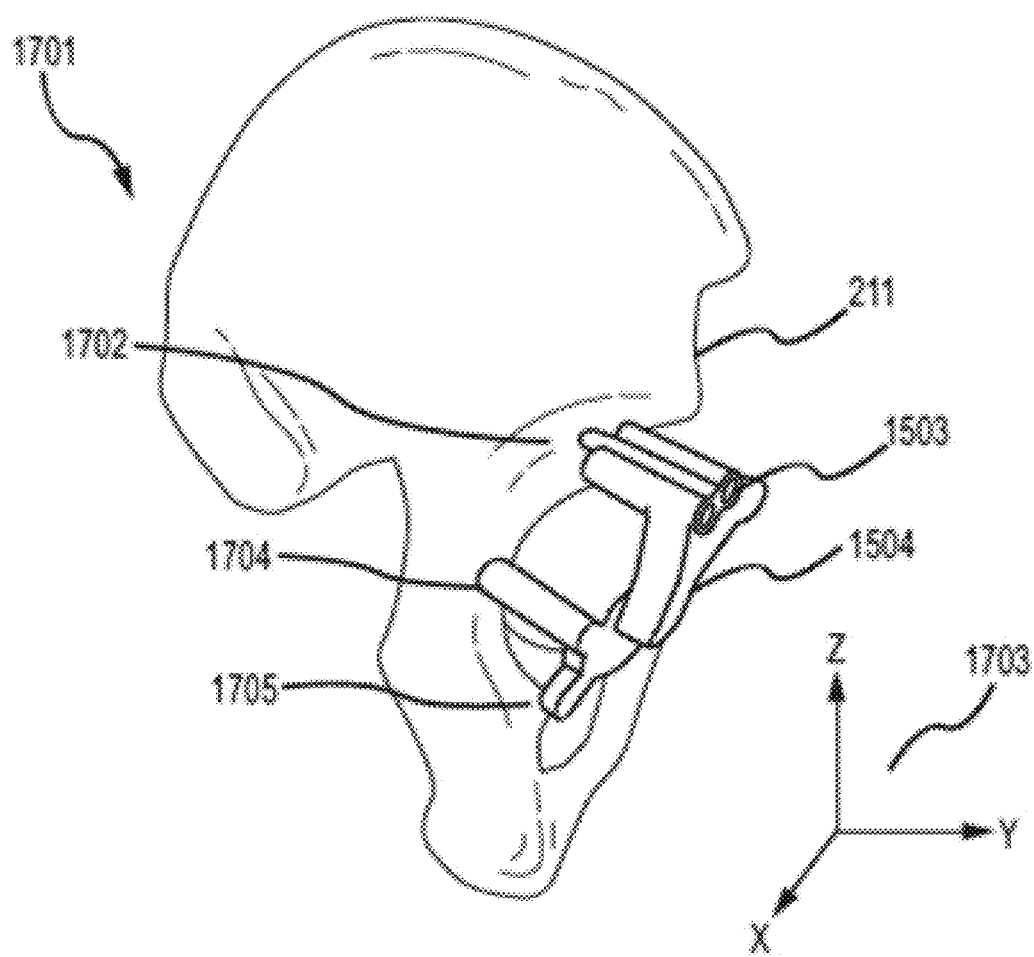
FIG. 17 is a posterior illustration showing the customized acetabular registration device mating to the patient's acetabulum with a frame of reference.

FIG. 17 is a posterior view of the pelvis with guide 1501 mounted to the acetabulum 1701. As mentioned above, the triangular body 1504 attached to the main circular body 1502 extends superiorly such that the two features 1523 and 1524 can reach the ilium body and notch below the spine 211. The cylindrical feature 1523 contacts the bone surface at location 1702. Note only a small space exists between the contact point 1702 and drill guide 1503 to prevent the drill from walking when the tip of the drill bit hits the hard bone at an angle. Also, arm 1604 extends downward to contact the acetabulum rim and inside the rim with the step-like circular feature at location 1704. The step-like feature of arm 1604 and 1606 prevent the guide 1501 from moving or shifting laterally. At least one or more step-like feature appears on the arms extending from the circular body. For example, arm 1605 may not include the step-like feature contacting the rim of the acetabulum at location 1705. As mentioned above, the customized acetabular registration guide may provide a 3D reference frame 1703 between the patient and robot so that the position and orientation of the acetabular component in the imaging data may be mapped to the patient's acetabulum during the procedure. Once the instantaneous registration and mapping are established, the robot or manual instrument can assist the surgeon to achieve the desired component trajectory and positioning.

Figure 18:
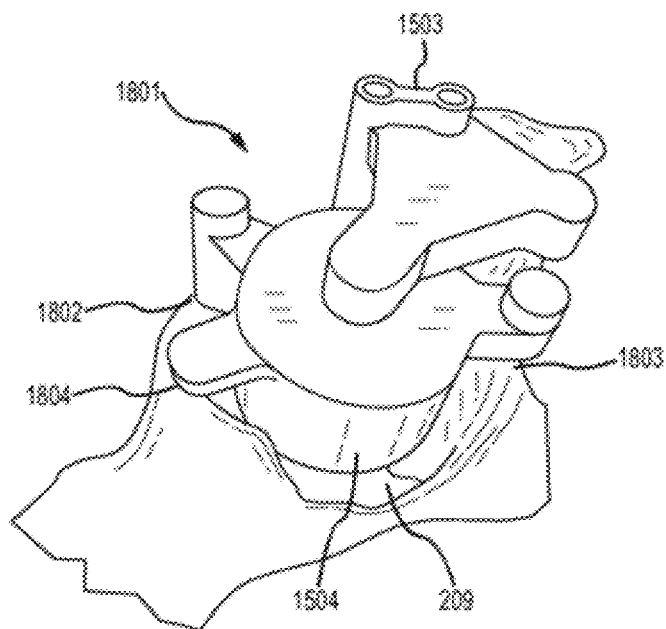
FIG. 18 is a perspective illustration of the customized acetabular registration device mating to the patient's bone.

FIG. 18 is an oblique view 1801 of the pelvis showing the acetabulum notch 209 with guide 1501 mounted on the acetabulum. As mentioned above, the three arms 1505, 1506, and 1507 extending from the circular body 1504 contact the rim at locations 1802, 1804, and 1803 respectively. The step-like feature of the arm 1505 and 1507 also contact inside the rim at location 1802 and 1803. The face (orientation) of the body 1504 represents the face (desired orientation) of the acetabular component 705. Using two drill bits or pins, the customized acetabular guide can be secured to the bone by drilling two pins using the rill guide features 1503 which represents a desired trajectory and position of the acetabular component. With these known references (frame of reference), the bone-mounted robot or manual instrument can achieve the desired trajectory during the reaming process in 603.

Figure 19:
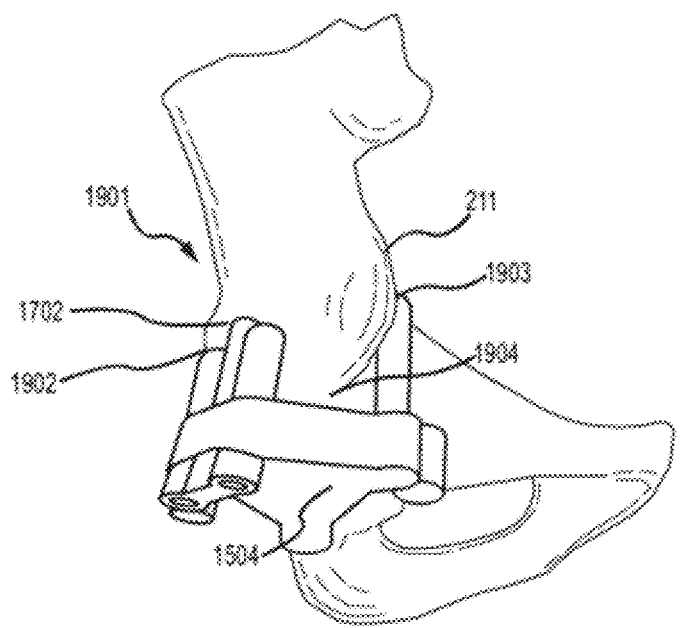
FIG. 19 is a perspective illustration of the customized acetabular registration device mating to the patient's iliac.

FIG. 19 is an oblique view 1901 of the pelvis showing the anterior inferior iliac spine 211 with guide 1501 mounted on the acetabulum. The triangular-shaped body 1504 of the guide 1501 comprises two elliptical features protruding posteriorly. Arm 1524 contacts the edge of the bone 1903 at the junction between the ilium and pubis bone. This prevents the guide from rotating counterclockwise. On the other side, the cylindrical feature 1523 contacts the ilium bone surface at location 1702. Note the location 1902 where the location of the two drill bits is one of the thicker parts of the pelvis bone. This location 1902 may provide a mounting location for the hexapod robot discussed in more detail below.

Figure 20A:
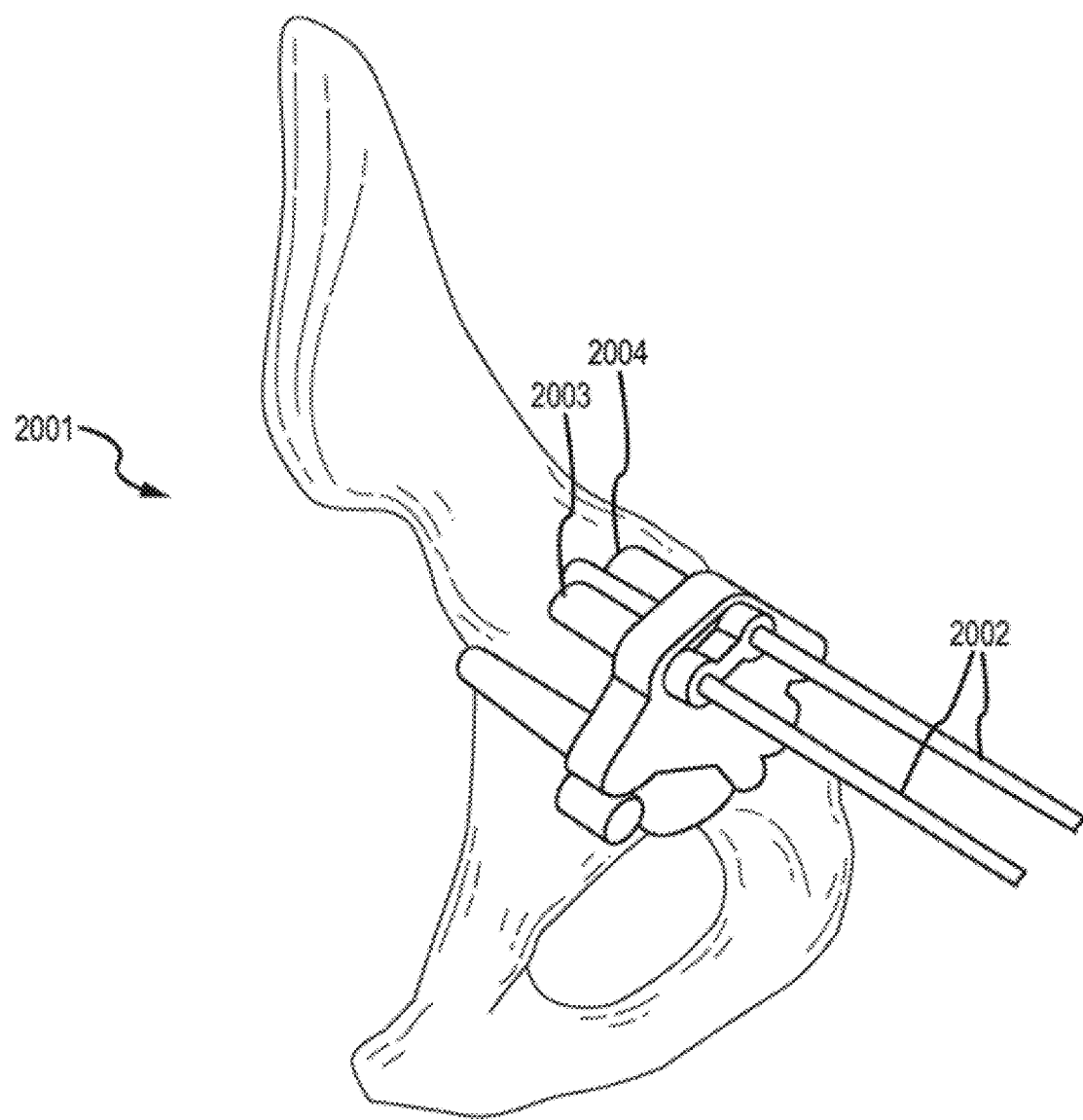
FIG. 20A is a perspective illustration of the customized acetabular registration device positioning two parallel pins secured to the bone.

FIG. 20A is a perspective view of the custom registration acetabulum guide 1501 with two pins 2002 inserted into the drill guide. The pins can be drill bits, screws, trocars, guidewires, or optical markers attached to the bone at locations 2003 and 2004. Once the open-ended pins are secured to the bone, the guide 1501 can be removed by sliding it away from the acetabulum. Once the guide 1501 is removed, robots, motion sensors, optical markers, or instruments can be attached to the pins as the desired position and orientation of the acetabular component. Changing the position and orientation of the acetabular component is straightforward once the initial trajectory/reference has been established. For manual instrumentation, the two drill bits 2002 can provide a line-of-sight (desired trajectory) reference for the surgeon using the acetabular reamer assembly 501. The desired trajectory can be achieved by aligning the reamer handle to the two drill bits by making sure they are close to parallel.

Figure 20B:
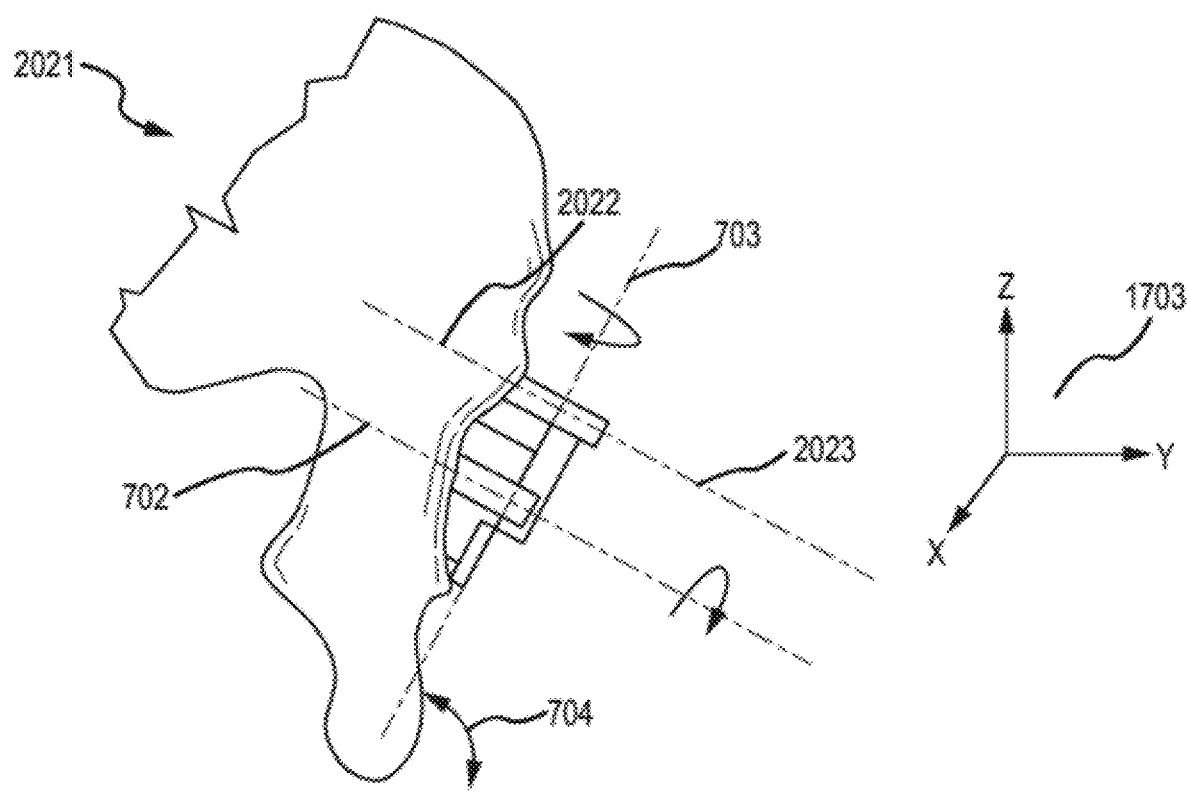
FIG. 20B is another perspective illustration of the customized acetabular registration device positioning two alignment pins secured to the bone with a defined coordinate system.

FIG. 20B is a perspective view of the pelvis with guide 1501 mounted on the acetabulum showing the various angular and offset relationships between the pins 2023 and the acetabular component. As mentioned above, the face of the guide 1501 represents the inclination or abduction angle 704. The center of the acetabulum and axis of rotation is represented by line 702 intersecting with line 703. Line 703 represents the face of the guide 1501 and also the version or anteversion angle. Line 2022 is parallel to the pins 2023 and perpendicular to line 703 at a known offset from the center of the acetabulum. The pins 2023 establish a known reference frame 1703 intra-operatively that can be mapped to the pre-op imaging data and robot's frame of reference. For a bone-mounted robot, the pins can represent the home/default position and orientation of the acetabular component.

Figure 21:
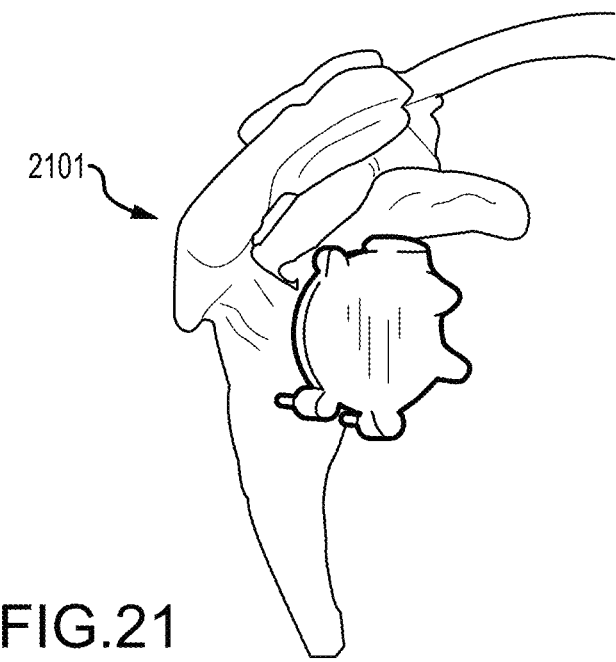
FIG. 21 is an illustration of a customized glenoid registration device mating to the patient's bone.
Figure 22:
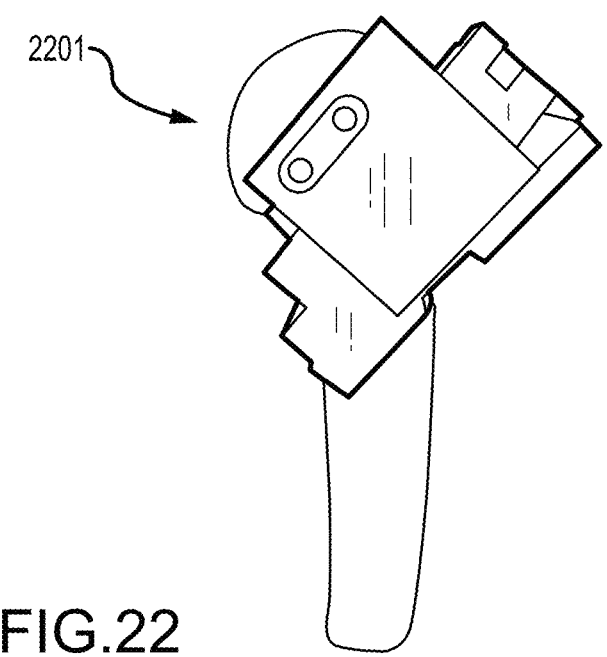
FIG. 22 is a top view of a customized humeral resection guide mating to a patient's bone.

As mentioned above, the customized resection and registration guides can be used in different joint arthroplasty procedures. FIG. 21 is an example of a customized glenoid alignment guide 2101 for shoulder replacement procedures. Similar to the acetabulum, the damaged bone of the glenoid fossa may be resurfaced/removed using a reamer connected to the hollow shaft of the handle and a guidewire representing the desired trajectory (orientation). The customized glenoid registration guide has similar mating shapes and drill and saw guide features as the customized acetabulum registration guide 1501. FIG. 22 is an example of a customized humeral resection guide for both standard and reverse shoulder prostheses. The head of the humerus and a portion of the neck are removed using an oscillating saw. For shoulder resurfacing procedures, the humeral head may be resurfaced similar to the femoral head surfacing in a partial hip replacement procedure. A guidewire or cylindrical dimple in the bone can be used as a reference for the desired trajectory when resurfacing the head. The humeral resection guide consists of similar mating shapes and drill and saw guide features as the customized femoral resection guide 1301.

As mentioned above, the customized acetabular registration guide provides two reference pins secured to the bone as one desired trajectory for the acetabular component. In order to determine the desired orientation of the acetabular component, imaging data can be used for pre-operative templating and planning. In one implementation, the orientation of the 2D imaging scan of the hip joint is approximately perpendicular to the femoral neck and head axis. To determine this orientation, the center point and face of the acetabulum may first be established using a series of 2D imaging slices. Once determined, the acetabular component can be placed in the "safe zone" for each patient. To aid in the description, FIGS. 23-26 describe in greater detail a method for identifying key anatomical landmarks from a series of 2D imaging to determine the desired acetabular component position and orientation. For ease of understanding, the discussion below is limited to the acetabulum but can be applied to other joints such as the shoulder, ankle, or elbow.

Figure 23:
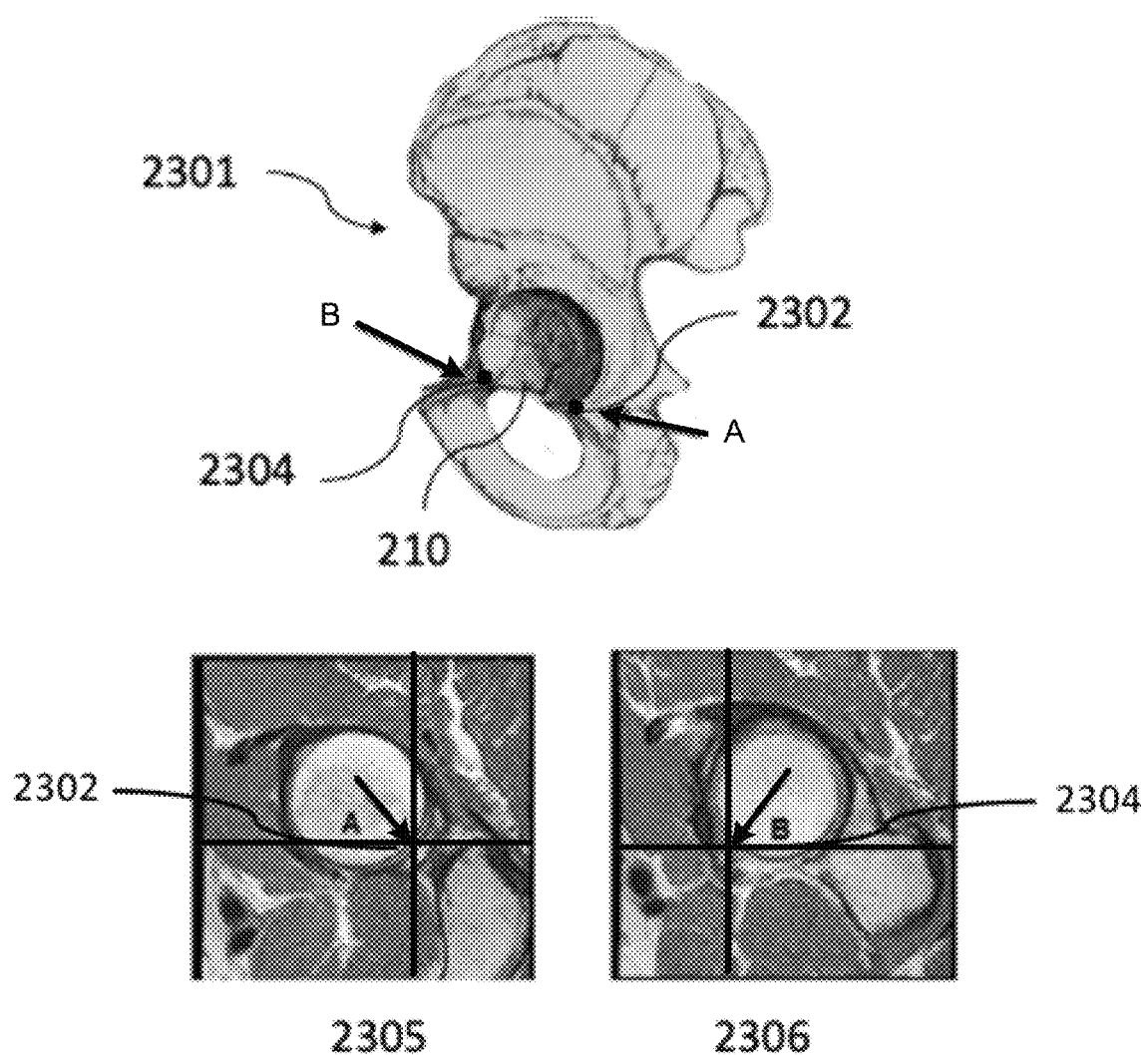
FIG. 23 includes illustrations of bony landmarks identified using scan images of the patient's hip.

FIG. 23 is an illustration of the pelvis 2301 and corresponding 2D imaging scans 2305, 2306 used to identify two anatomical landmarks near the notch of the acetabulum 209. Point A is located on top of the acetabular surface at the mid-point of obturator groove of the pubis. Point B is also on top of the acetabular surface at the mid-point of pubis spine. As shown in the 2D sagittal imaging scans, points A and B can be easily identified in 2D imaging slices 2305 and 2306, respectively, at locations 2302 and 2304 at the point in the scans in which the bone is barely protruding.

Figure 24:
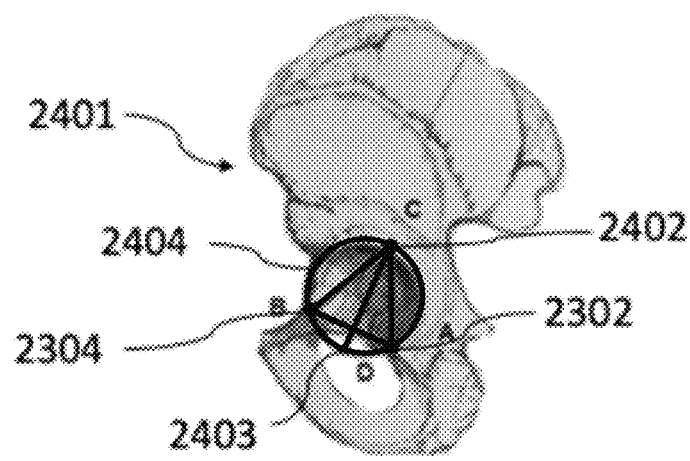
FIG. 24 includes illustrations of additional bony landmarks identified using scan images of the patient's hip to define a plane and centerline.
Figure 24:
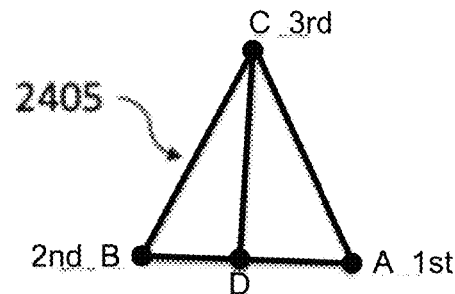
Figure 24:
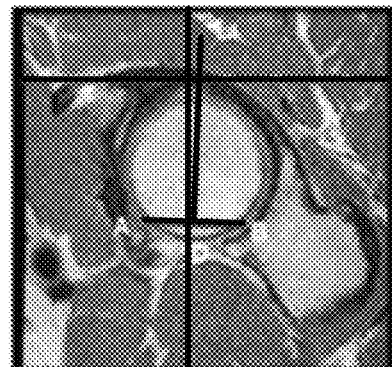
Figure 24:
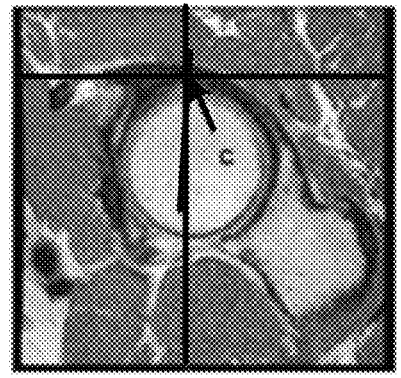

FIG. 24 is an illustration of the pelvis 2401 and corresponding 2D imaging scans used to identify a third anatomical landmark to establish the orientation (face) of the acetabulum 210. As discussed above, point A 2302 and point B 2304 are established from the sagittal 2D imaging scan and the corresponding cartesian coordinates (x, y, z). Point D 2403 may be identified as the mid-point of line A-B. A perpendicular line relative to line A-B can be projected at point D 2403 superiorly as shown in image 2406. The perpendicular line intersects at the third contact point C 2402 located at the acetabular rim, which can be easily identified in image 2407. The three points A, B, and C form a triangle 2405 where line BC is equal to line AC, line BD is equal to line AD, and angle BCD is equal to angle ACD.

Figure 25:
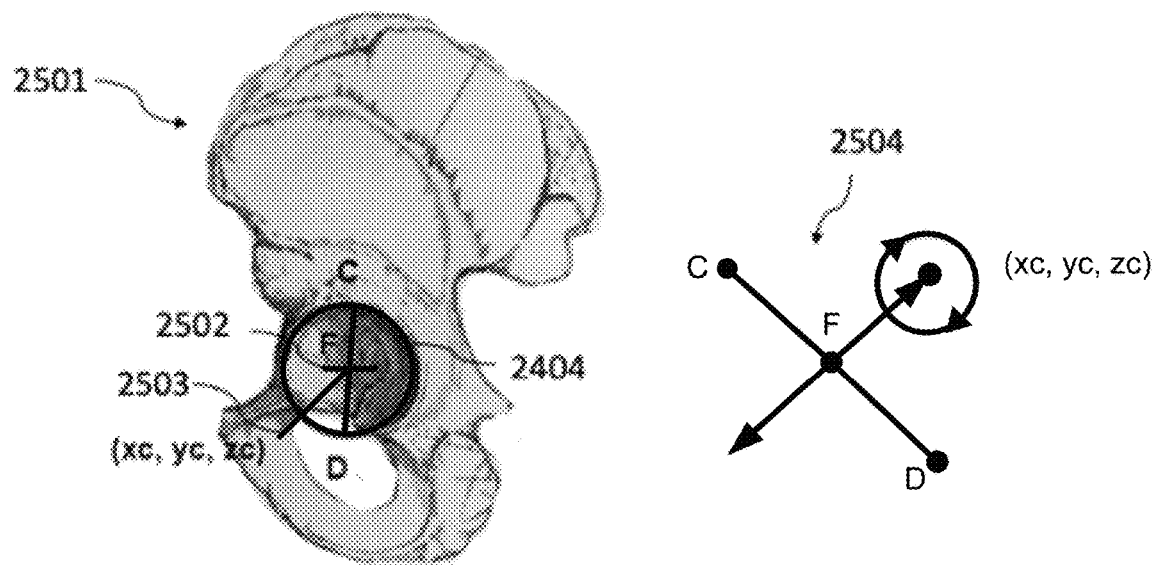
FIG. 25 is an illustration of an acetabular plane and center point of the patient's hip used to define an anatomical coordinate system for positioning the cup prosthesis.

FIG. 25 is an illustration of the pelvis 2501 showing the hip center point F 2502 and axis of symmetry 2503 of the acetabulum 210. This line 2503 represents the trajectory of the acetabular reamer and point F 2502 represents the center position of the acetabular component. The spherical acetabular reamer 2404 rotates about line 2503 at the center point F 2502 and line CD represents the orientation of the acetabular component. As discussed above, the desired acetabular component inclination is about 40° of abduction relative to the floor or about 15° relative to the anatomical face of the native acetabulum.

Figure 26:
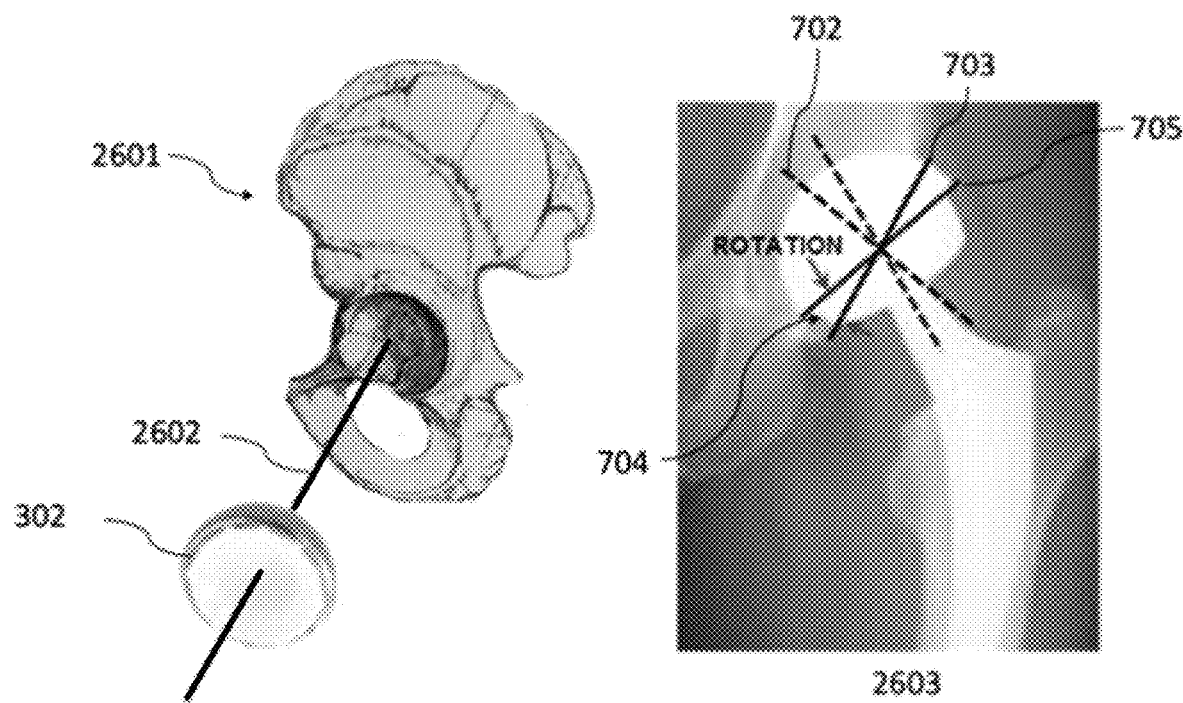
FIG. 26 is an illustration of an acetabular prosthesis with an axis of rotation and an anatomical coordinate system to define the cup orientation.

FIG. 26 is an illustration of the acetabular implant position of the hip joint 2601 after implantation as shown by the post-operative x-ray 2603. Line 2602 is the desired trajectory of the acetabular impactor when the component is press-fitted to the bone. From the patient's anatomical axis of rotation 702, the desired trajectory of the acetabular component is abducted about 15°, as shown by the arrows 704. This may be included because the acetabular component has a semi-spherical design whereas the natural acetabulum is less than semi-spherical, which may cause impingement between the shell and neck of the stem inferiorly and possible dislocation.

As discussed in detail above, an anatomical approach for orienting and positioning the acetabular component using a series of 2D imaging of the is disclosed. Aspect of the present disclosure may also involve methods and systems for a surgical planning software that allows the surgeon to dictate the desired implant size, orientation, and position for each patient using a series of 2D imaging scans. To aid in the description below, a brief discussion of the controls and an example graphical user interface (GUI) is described. As mentioned above, the present disclosure may be applied to any joint as part of the orthopedic procedure. However, for ease of understanding, the discussion herein is limited to particulars of the hip as an example of the inventions relating to the present disclosure procedure and embodiments.

Figure 27:
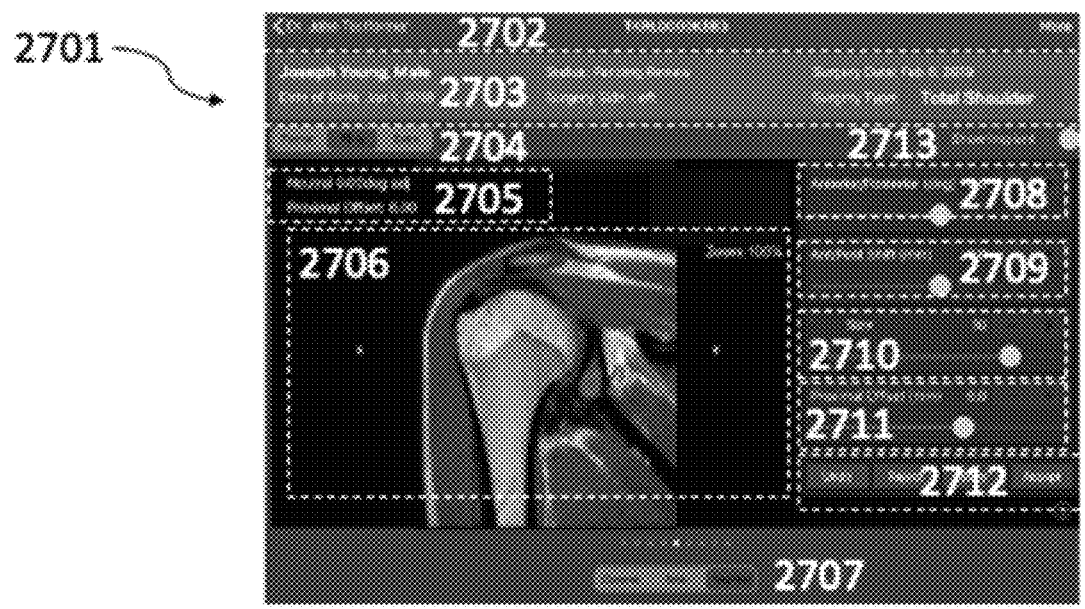
FIG. 27 is an illustration of pre-operative planning software on a mobile computing platform.

FIG. 27 illustrates a screenshot of a user interface 2701 a surgical planning software for use in hip replacement surgery and displayed on a display device in communication with a computing device. The user interface 2701 may display 2D imaging data in one, two, or three planes (i.e., 3D scans) or 3D models (i.e., bone and/or implants) in 2706 for a particular patient undergoing the hip replacement procedure. Starting with 2702, a surgeon's name and Case ID may be displayed on top of the computing device. Underneath 2702 may be the patient and surgery information 2703 including name, date of birth, operative side, procedure type, and process status. Portion 2704 of the user interface 2701 allows the surgeon to select the surgery planning for a particular portion of the bone, such as femur or pelvis, or review any display of interest or relevance not part of the imaging data. For example, the surgeon can view and adjust the implant position displayed in 2705 and size 2710 of the femoral stem follow by the acetabulum size. The implant positioning and size can be adjusted independently by making the implant invisible using the show implant button 2713. Both angular and displacement can be adjusted using slide controls in 2708-2709 and 2711, respectively for a particular plane (i.e., coronal, axial, sagittal). To view 2D images in different planes or 3D models, the user interface controls in 2707 allow the surgeon to select the desired images. Also, the series of 2D images may be viewed sequentially by scrolling the images one at a time. In one embodiment, all 3 orthogonal images are displayed simultaneously in a grid format (i.e., 1×2 or 2×2). Once the surgeon completes the surgical planning review, the options in 2712 allow the surgeon to approve, reject, save, or undo the case. If the case is approved, the surgical planning information may be sent to the robot or network before the start of the procedure.

Aspects of the present disclosure involve methods and systems for a robotic-assisted surgical system mounted to the patient's anatomy. To aid in the description below, a brief discussion of the hexapod geometry, forward and inverse kinematic equations, range of motion, and workspace. A hexapod, also called the Stewart platform, is a type of parallel robot that has 6 prismatic actuators, usually with hydraulic jacks or electric linear actuators, attached in pairs to three positions on the top plate and baseplate. As mentioned above, the present disclosure may be applied to any region of a patient's joint as part of the orthopedic procedure. However, for ease of understanding, the discussion herein is limited to hexapods for the hip as an example of the disclosures relating to the present disclosure procedure and embodiments. Any robot configuration (i.e., free-standing or bone mounted) and any degrees-of-freedom (DOF) robot can be used to guide the reamer during the preparation of the acetabulum in hip replacements.

One of the advantages of the hexapod is that it is stiffer and more compact compared to a conventional robot of the same DOF due to its parallel geometry. This may aid in achieving the accuracy needed in precise implant positioning when reaming dense bone caused by osteoarthritis. The geometry of the hexapod system comprises two platforms (top plate and base plate), parallel manipulators attached in pairs to three equally spaced positions on the platform's base plate, crossing to three-mounting points on the top plate. All 12 connections are made via universal joints. Devices, such as the reamer, ball mills, drill bits, or other tools attached to the top plate can be moved in all 6-DOF: 3 linear movements X, Y, Z (lateral, longitudinal, and vertical) and the 3 rotations (roll, pitch, and yaw, which can be described by forward kinematic equations and inverse kinematic equations). The robot's range of motion can be described by a cube-like volume spanned by the corner point 1 to 8. Those of ordinary skill in the art will understand the hexapod geometry and advantages of using a hexapod-based robotic device.

Figure 28:
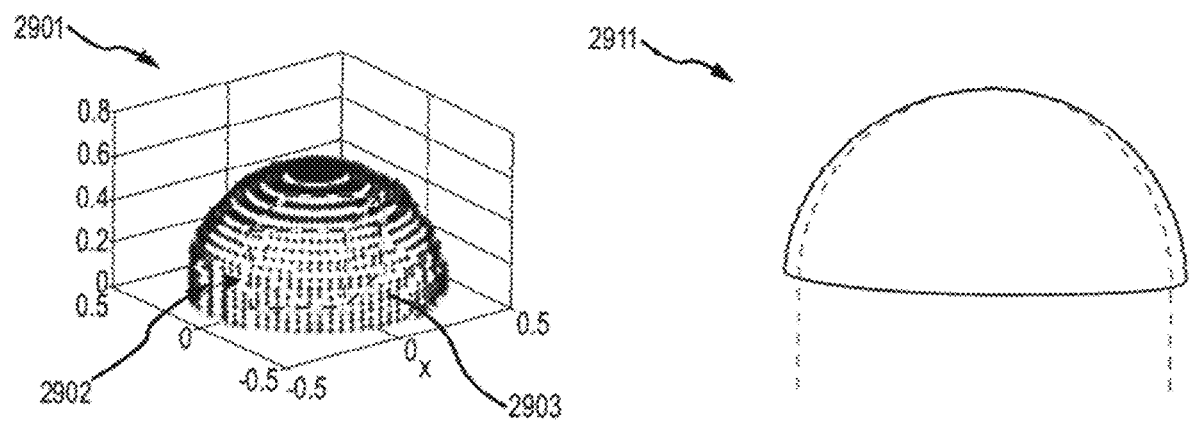
FIG. 28 is an illustration of a hexapod workspace and shape of an acetabular component shell.

FIG. 28 is an example of the hexapod robotic device 3D workspace 2901. As described above, the top plate may be moved in all 6 DOF limited by the robot's range of motion described by the cube-like volume 2902. The spherical workspace of the top plate 2902 is similar to the geometry of the shell of the acetabular component 2911. This may be ideal for a bone mounted robot for milling the cavity of the acetabulum due to its compact design and stiffness. Also, the hexapod geometry is especially suited for minimally invasive surgery (MIS) techniques, such as direct anterior, posterior, or anterolateral approach, as the robot can be mounted on the outside of the patient's body. In some instances, only the tool, such as the acetabular reamer or ball-shaped milling tool, is located inside the body.

Figure 29:
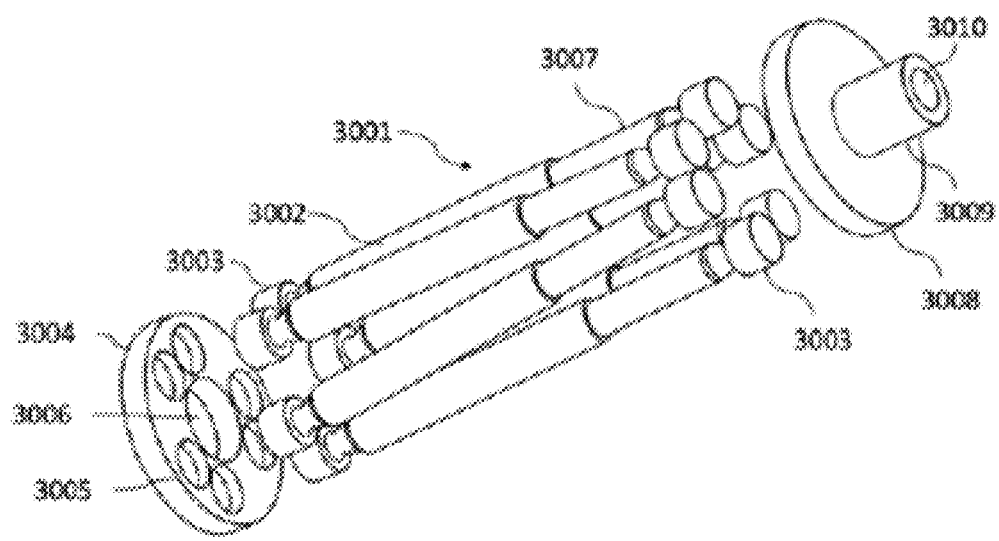
FIG. 29 is an exploded view of a 6-degrees of freedom hexapod robot.

FIG. 29 is an exploded view of an example hexapod robot in 3001 for use in hip replacement surgery. As discussed above, the hexapod robot 3001 comprises a base plate 3004 and top plate 3008 and prismatic joints 3002 in the form of linear actuators 3007. One end of the linear actuator 3007 is connected to the base plate in pairs 3005 via universal, spherical, or revolute (ball) joint 3003 or any combination. Similarly, the other end of the linear actuator 3007 is connected to the top plate 3008 via a universal joint. Near the center of the base plate 3004 is a circular or elliptical through-hole 3006 that accommodates the reamer shaft allowing it to move, orient, or rotate freely. In one embodiment, the diameter of the circular hole 3006 is approximately the same as the largest acetabular component size. This would allow the robot to mill the bone using linear movements in X, Y, and Z axes. In another embodiment, the base plate through-hole 3006 has an open slot that extends beyond the edge of the base plate allowing quick tool change outside the body. The through-hole 3006 in the base plate 3004 allows the robot to orient the acetabular reamer and shaft in the desired trajectory for a certain surgical approach. A similar though hole 3010 is located near the center point of the top plate 3008. The diameter of the through-hole 3010 can be the same or larger than the diameter of the reamer shaft. A collet, clamp, or circular jaw vise 3009 can be used to secure the reamer shaft sleeve or handle while the shaft is allowed to rotate freely. In one embodiment, the acetabular reamer is located on the outside of the robot 3001 and secured to the top plate using an outrigger attachment. This attachment may be an extension of the top plate 3008 or a separate mechanical fixture attached to the top plate. In general, one or more tools and/or instruments can be attached to the hexapod's top plate.

Figure 30:
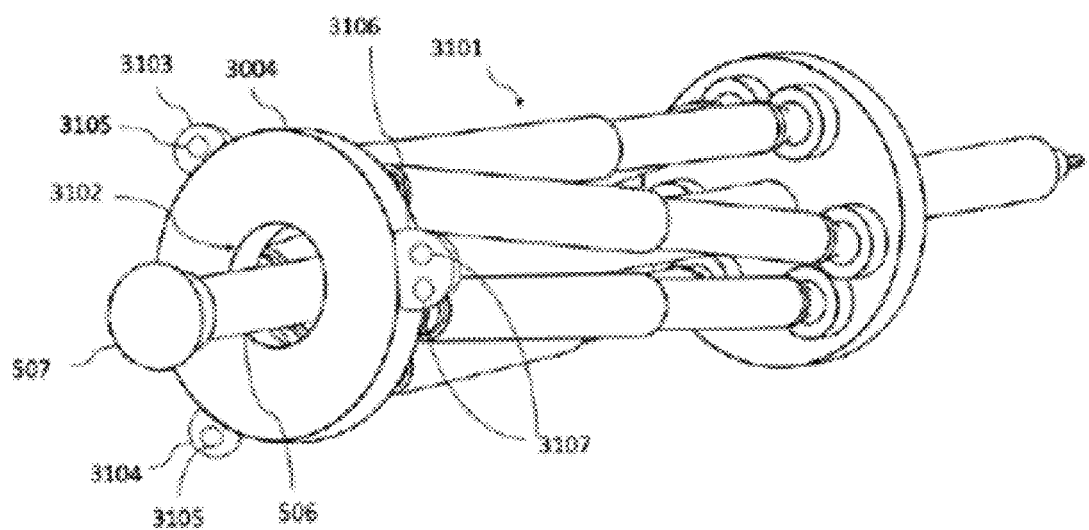
FIG. 30 is an illustration of an example of an acetabular reamer connected to a hexapod robot with pinholes for mounting to a patient's bone.
Figure 31:
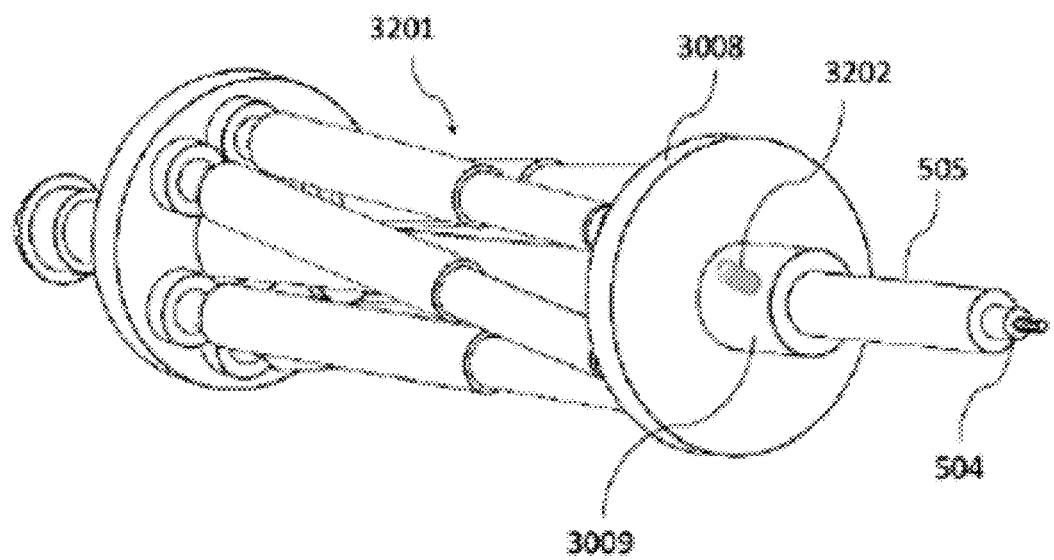
FIG. 31 is an illustration of an example of an acetabular reamer connected to a hexapod robot's top plate and secured to a collar.

FIGS. 30-31 are isometric views of the hexapod robot 3001 with reamer handle 505, shaft 506, and acetabular reamer 507 extending through the center hole 3102 of the base plate 3004 and top plate 3008. As discussed above, the top plate 3008 shown in FIG. 31 can move in all 6 DOF while the base plate 3004 shown in FIG. 30 is stationary (i.e., secured to the pelvis using fixation pins, trocars, screws, etc.). To mount the hexapod robot 3001 to the pelvic bone, external attachment points 3103, 3104, and 3106 are used for fixation and positioning the robot for reaming the acetabulum. As discussed above, the custom acetabular registration guide sets the position and orientation of the acetabular component using two-parallel pins 2002 attached near the anterior inferior iliac spine 211. Attachment point 3106 may include two holes in 3107 that are the same diameter and spacing as 2002. One or more additional attachment points 3103 and 3104 may be used to stabilize the robot relative to the initial acetabulum component determined during pre-operative planning. The three attachment points 3106, 3103, and 3104 form a tripod configuration where 3106 is near 211 and 3103 can be located near 207 and 3104 near 204. In FIG. 31, the top plate 3008 may hold the reamer shaft handle 505 using a collet 3009 and locking screw 3202, with the external attachment points comprising at least one hole or open slot 3105 and collet or vise to hold the instrument or device to stabilize the robot during reaming. The base plate 3004 may be an extension of the prismatic joints of the hexapod. In one embodiment, each pair of linear actuators 3002 and universal joints 3003 may be attached to the pelvic bone directly eliminating the need for a base plate. In another embodiment, a mechanical fixture may be attached to the bone initially. The robot 3001 is then mounted to the mechanical fixture for ease of assembly and disassembly. The default position of the fixture can be determined using computer navigation systems or manually using conventional instrumentation and can be adjusted manually the position and orientation of the fixture using anatomical landmarks as reference.

Figure 32:
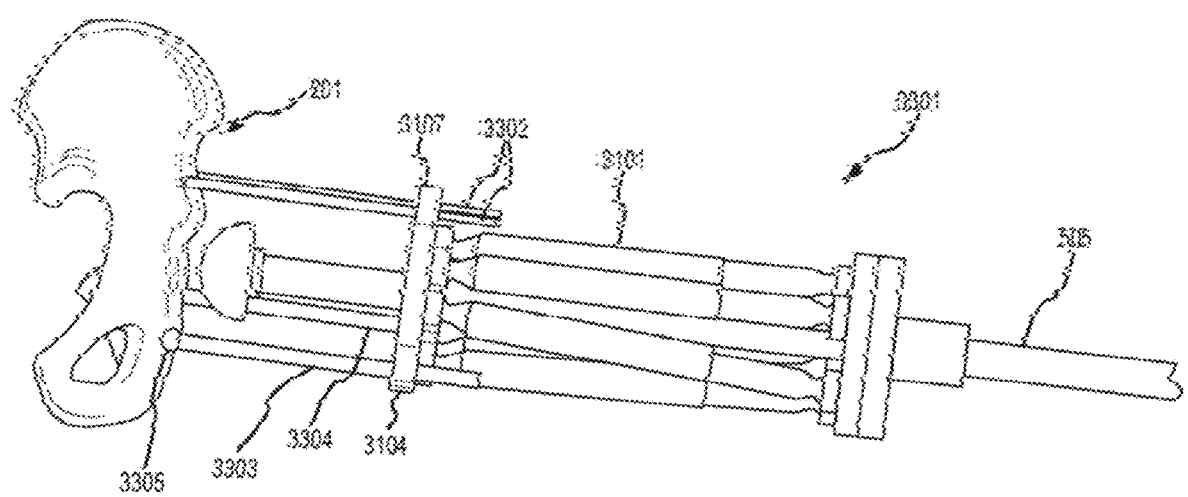
FIG. 32 is a perspective illustration showing the bone-mounted hexapod robot orienting the acetabular reamer at the desired trajectory.

FIG. 32 is an isometric view 3301 of the hexapod robot 3101 attached to the pelvic bone 202 using attachment points 3103, 3104, and 3107 and pins 3302, 3303, and 3304. The attachment pins can be drills bits, screws, trocars, or spherical feet 3305 that rest on the bone. At least one fixation point is used to position and orient the hexapod robot 3101 to the bone 202 as part of the registration process using the custom acetabular guide. In some instances, it may be undesirable to create additional fixation holes in the bone due to poor bone quality, fractures, or infections. In one embodiment, the handle of the shaft inside the collet is free to translate along the acetabular component axis of symmetry. The hexapod robot 3001 may therefore be assisting the surgeon by guiding the reamer or impactor in the desired trajectory. This allows the surgeon to control the depth of reaming and impaction manually. As discussed above, different surgical approaches and surgical techniques may be used during hip replacement procedures. To accommodate these differences, dedicated instrumentation has been developed, such as an offset handle for the acetabular reamer. The present disclosure can also accommodate the different surgical techniques and approaches by mounting the robot at different locations on the pelvis and using an outrigger attachment holding the acetabular reaming tool at the desired trajectory.

Aspects of the present disclosure also involve methods and systems for controlling robotic-assisted surgical systems using force/torque sensors as feedback (i.e., control, haptic, speed, and force) for reaming or milling different bone qualities. To aid in the description below, a brief discussion of the issues related to reaming a damaged acetabulum or sequential reaming, a torque/force sensor mounted on the top plate of the hexapod, and an intelligent control system for milling or reaming bone manually or automatically following a pre-planned toolpath are now included. As mentioned above, the present disclosure can be applied to other joints including the shoulder and spine. For ease of discussion, the detailed discussion below is focused on hip replacement surgery.

Figure 33:
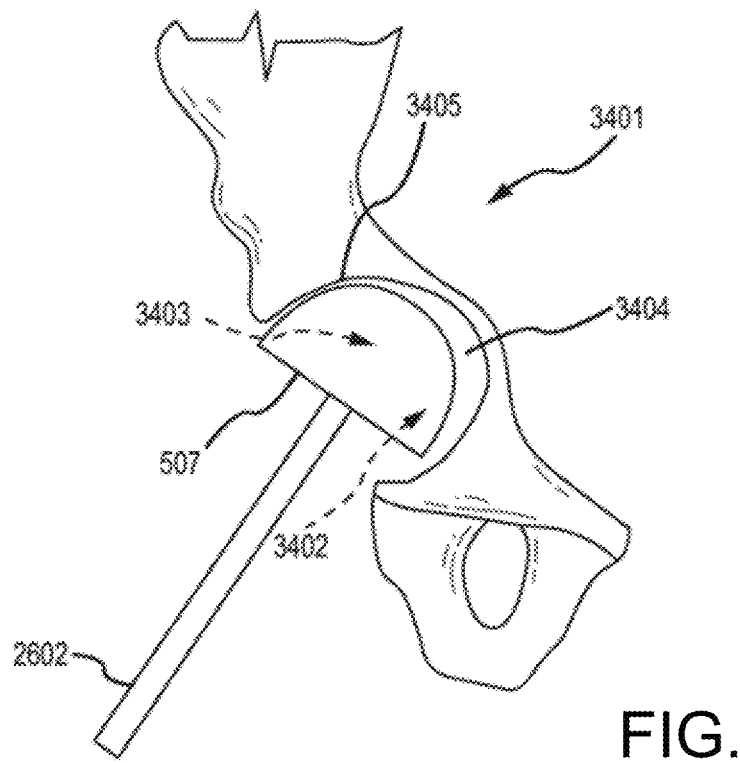
FIG. 33 is a perspective illustration showing the reaming trajectory and lateral forces deviating from the desired position due to damaged bone inside the acetabulum.

FIG. 33 is a lateral view of the acetabulum showing the trajectory of the acetabular reamer 3402 during the reaming process. As discussed above with reference to FIG. 6, the manual reaming process usually starts with a smaller size working up towards the target size. Due to damage (loss of cartilage and bone) inside the acetabulum 3404, the hip joint may not fit tightly together like a normal ball-socket joint, thereby increasing the friction inside the diseased joint due to the loss of hydrodynamic joint fluid lubrication. This increase in friction can cause uneven and excess bone wear 3404, which may create a pocket within the socket. Due to the spherical shape and smaller sized reamer, the initial bone contact point 3405 causes the acetabular reamer 507 to wander (deviate) from its planned trajectory (along the shaft handle 2602) along the path of least resistance 3403. One solution to prevent the acetabular reamer from deviating is to provide a guidewire drilled into the center point of the acetabulum. This is generally not ideal, however, as the walls of the acetabulum may be rather thin due to wear and not able to support the guidewire. A better solution may be to orient the trajectory of the reamer handle perpendicular to the contact point 3405, thereby removing the undamaged bone first until the pocket 3404 disappears when the cup becomes spherical. In one embodiment, the acetabular reamer 507 may contact at 3405 while the reamer handle 2602 is oriented at the desired trajectory. This may include the surgeon adjusting the position or orientation of the desired trajectory manually without any reference or feedback regarding the bone quality or damage.

Figure 34:
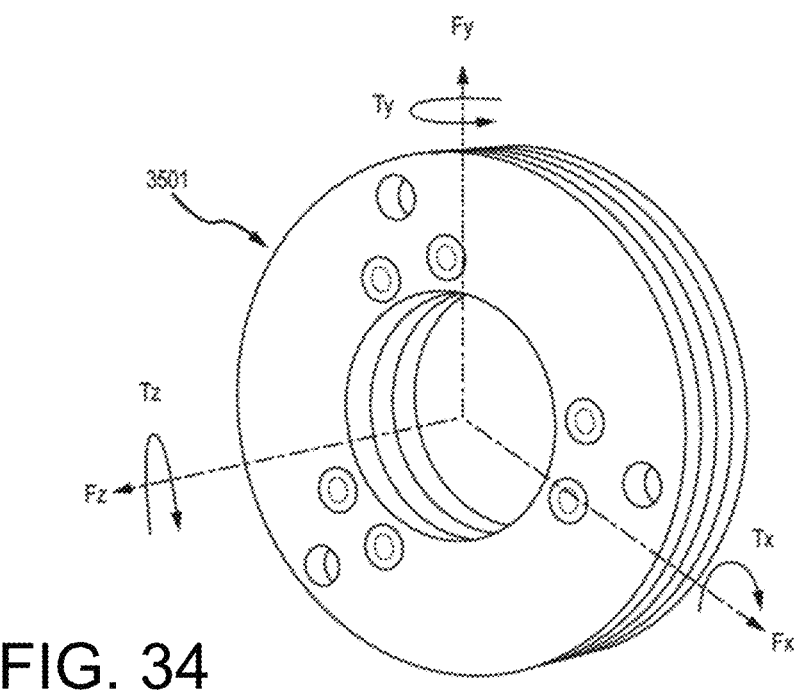
FIG. 34 is a perspective illustration of a force/torque sensor with defined coordinate system.
Figure 35:
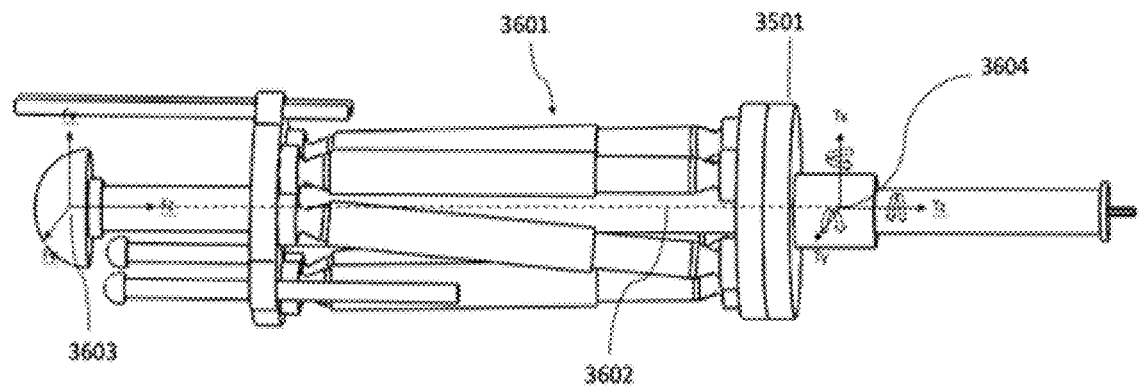
FIG. 35 is a perspective illustration of a force/torque sensor with defined coordinate system for a hexapod robot and acetabular reaming tool.

As discussed above, preventing the acetabular reamer from deviating from the desired position or orientation is challenging even for the most experienced surgeon. To address this problem, a torque/force sensor may be used to detect any deviation 3403 from the desired trajectory 3402, as well as bone quality. In FIG. 34, a force/torque sensor 3501 is shown that may be used to detect any deviation (i.e., magnitude and direction) of the desired trajectory. The circular shape sensor with a center hole utilizes strain gauges mounted at various locations inside the metal housing to detect force and torque along the X, Y, and Z axes. The sensor may also include 6 DOF, meaning that it can detect linear forces along the X, Y, and Z axes and torques or moments along each X, Y, and Z axes. The sensor 3501 can be mounted to the hexapod robot 3601 sandwiched between the top plate and the collet, illustrated with reference to FIG. 35. The center circular hole of the sensor is larger than the diameter of the reamer shaft handle to prevent any interference.

In one embodiment, the origin of the force axes 3603 is the same as the center point of the acetabular reamer. In general, the origin of the force vectors (Fx, Fy, and Fz) can be defined anywhere along the reamer shaft axis 3602. Similarly, the origin of the torque vectors (Tx, Ty, and Tz) 3604 can be defined at the center of the sensor. Also, the origin of the torque vector (Tx, Ty, and Tz) can be defined anywhere along the reamer shaft axis. As discussed above, the magnitude and direction of the deviation can be detected and corrected using 3501. Any correction can be done automatically via the robot's feedback controller or manually by notifying the surgeon in the form of haptic feedback. For example, the amount (force) and direction (moment/torque) of the deviation can be converted into resistance, vibrations, or sounds to the operating surgeon. This feedback information would allow the surgeon to make the necessary adjustments to correct the deviation before a larger pocket is created.

Figure 36:
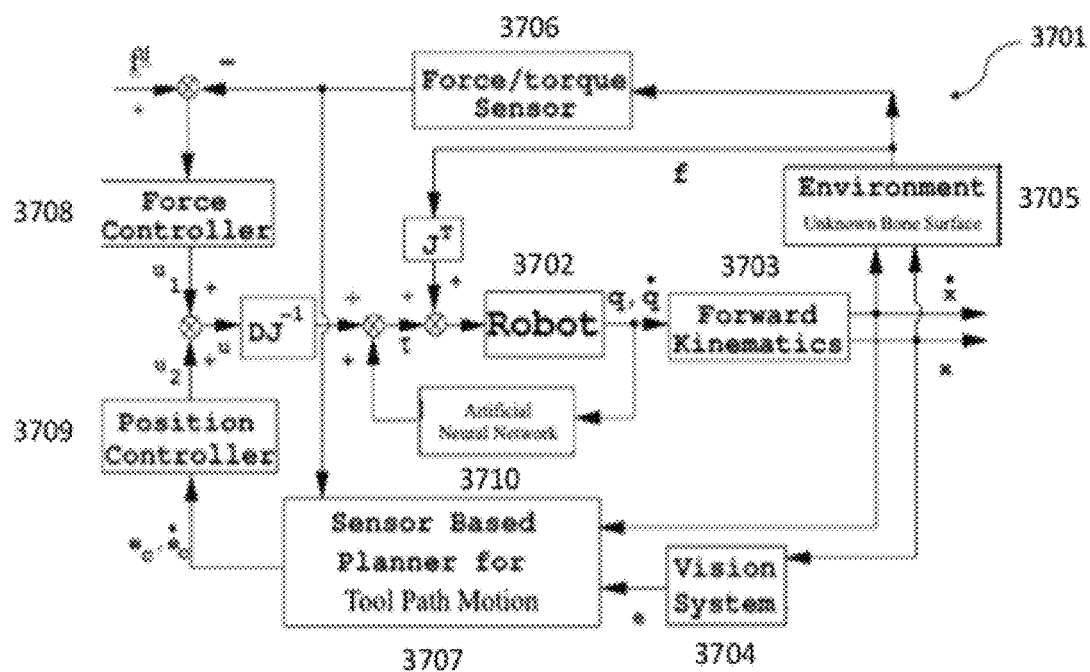
FIG. 36 is a block diagram of an intelligent robotic control system using a force/torque sensor for feedback control and tool path compensation for an unknown bone surface.

FIG. 36 is a block diagram of an intelligent robot control system 3701. Starting with 3702 is the robot dynamic equations follow by the forward kinematics equation 3703. As discussed above, the hexapod forward kinematics may include inputs q and q_dot where q is a vector describing the angular position and q_dot vector is the angular velocity, with the corresponding outputs being x and x_dot where x is the position vector and x_dot is the velocity vector of the top plate. The bone surface/quality in 3705 is modeled as an unknown environment since it is impossible to model the bone quality for each patient. The output of 3705 can be described in terms of force (f) vectors since the inputs are the position (x) and velocity (x_dot) of the acetabular reamer making contact with the bone surface. The force/torque sensor 3706, as discussed above, senses the force and torque vectors of the acetabular reamer. The outputs of the 3706 are then compared to the desired force (f d) and the difference (error) is fed into the force controller 3708. The second feedback path uses a vision system 3704, such as computer navigation, to track the tool (acetabular reamer) path. For manual reaming, this feedback is not necessary. Similarly, the vision system 3704 may not be needed if the initial position and orientation can be established using the custom acetabular registration guide. The sensor-based planner for tool path motion 3707 is used with a milling system, similar to CNC machines. A single ball mill can be used to remove the damaged cartilage/bone without the need of using different size reamers. The outputs of the force sensor may be used to compensate or correct for tool deviation from the desired trajectory. This error (desired vs. actual) compensation is used for tool path motion trajectory. The outputs of 3707 are the error (e) and error velocity (e_dot) vectors, which then fed into the position controller 3709. The outputs of 3708 and 3709 may be combined to produce a single (u) which is then mapped to produce a torque vector (tau). The output force vector from 3705 can be mapped as an unknown torque disturbance added to the torque input (tau). Finally, the robot's feedback controller 3710 can be either a linear or non-linear controller. Linear controller, such as PID (proportional, integral, and derivative), may include precise modeling of the environment and robot dynamic equations. A non-linear controller, such as an artificial neural network or fuzzy logic, can be used to compensate for the unknowns in the system.

Figure 37:
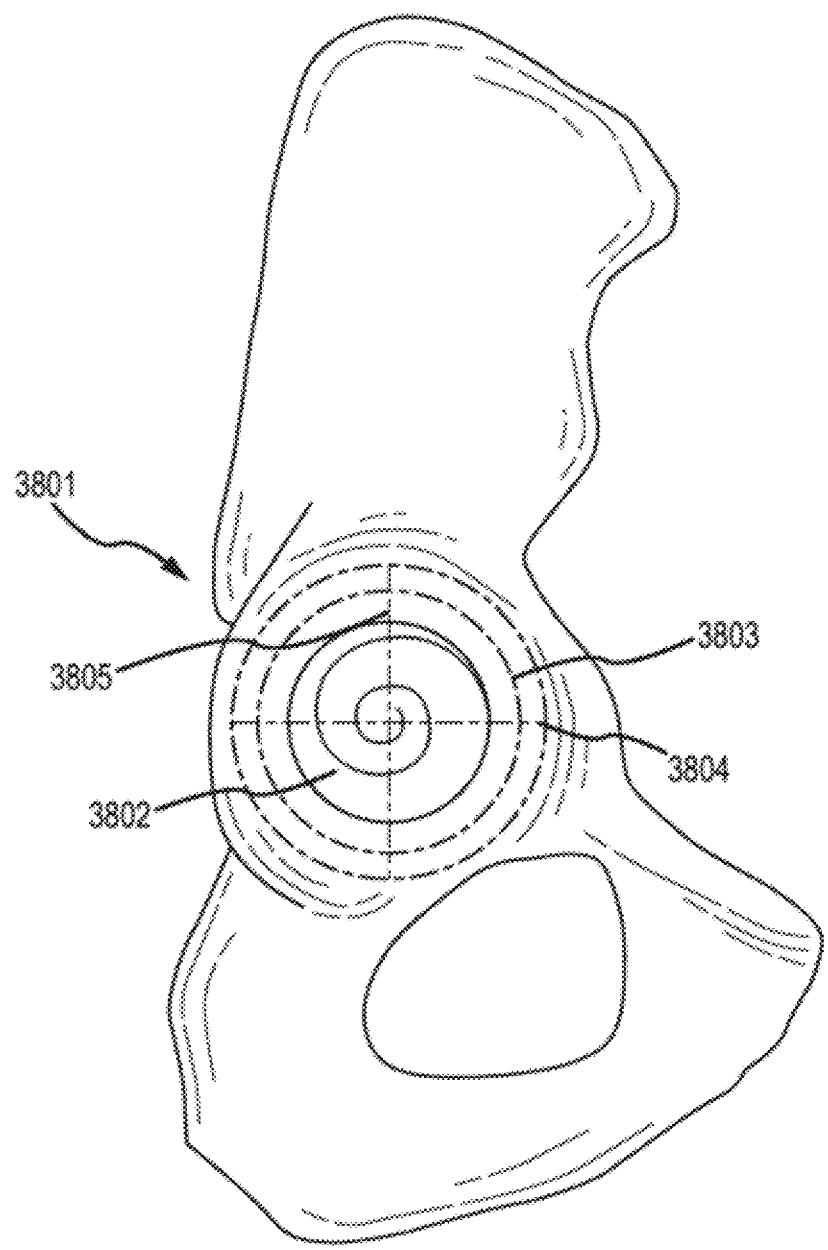
FIG. 37 is an illustration of various tool paths for reaming the acetabulum using a ball-shaped milling tool.

FIG. 37 illustrates the tool path of a ball-shape mill for removing the damaged acetabulum bone and replace with an acetabular component. Ball-shape mills are generally spherical and come in different sizes (diameters). The advantage of milling instead of sequential reaming is that only a single tool is needed during the procedure. Also, the tool path can be programmed to accommodate different size and shape (spherical versus elliptical) components as well as custom acetabular components. Tool path profile can be spiral 3802, circular 3803, or linear along 3804 or 3805 or any combination to optimize the tool path based on the shape of the artificial cup. The tool path can be pre-programmed and stored in the robot's computer. Once the surgeon has determined the desired cup size, the corresponding tool path can be transmitted to the robot's controller.

Aspects of the present disclosure involve methods and systems robotic-assisted surgical systems for joint replacements. To aid in the description below, a brief discussion of integrating the force/torque sensor for closed-loop control in real-time, using a vision system, such as computer navigation and vision systems, for tool path, patient registration, and motion tracking and milling the acetabular cup automatically based on the tool path of the target implant size. As mentioned above, the present disclosure may be applied to any region of a patient's joint as part of the orthopedic procedure. However, for ease of understanding, the discussion herein is limited to robotic-assisted surgical systems for the hip and shoulder as an example of the inventions relating to the present disclosure procedure and embodiments. Any robot configuration (i.e., free-standing or bone mounted) and any degrees-of-freedom (DOF) with a sensor attached to the end-effector to guide the reamer during the preparation of the acetabulum or glenoid.

Figure 38:
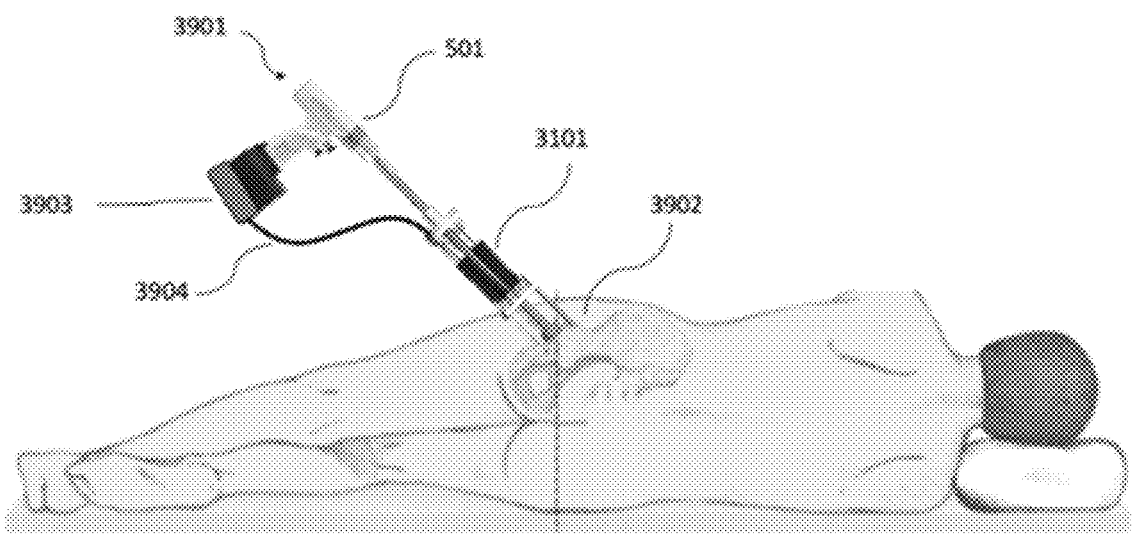
FIG. 38 is an illustration of a patient undergoing hip replacement surgery using a bone-mounted robot and hand-held power tool with a robot feedback controller.

FIG. 38 is an illustration of a patient undergoing hip placement surgery in 3901 using a bone mounted hexapod robot 3101 and a micro-controller or computer 3903 for processing real-time data from the force/torque sensor. As discussed above, the robot may include a default position determined by the customized acetabular registration guide using two pins located at 3902. The other two attachment points (3103 and 3104) as part of the tripod can be attached to the bone by drilling the pins through the skin. The exact location and orientation vary as the attachment pins are for stabilizing the robot. A force/torque sensor can be used to measure and transmit real-time data using a wired or wireless communication 3904 to the robot controller 3903. This real-time data can then be used as feedback robot control and tool-path correction. In this example, the surgeon is controlling the power drill 501 manually while the robot 3101 is controlling the desired trajectory and depth. The robotic-assisted surgical system of 3901 is completely self-contained. If additional power is needed, a wired cable can be connected to the robot's controller.

Figure 39:
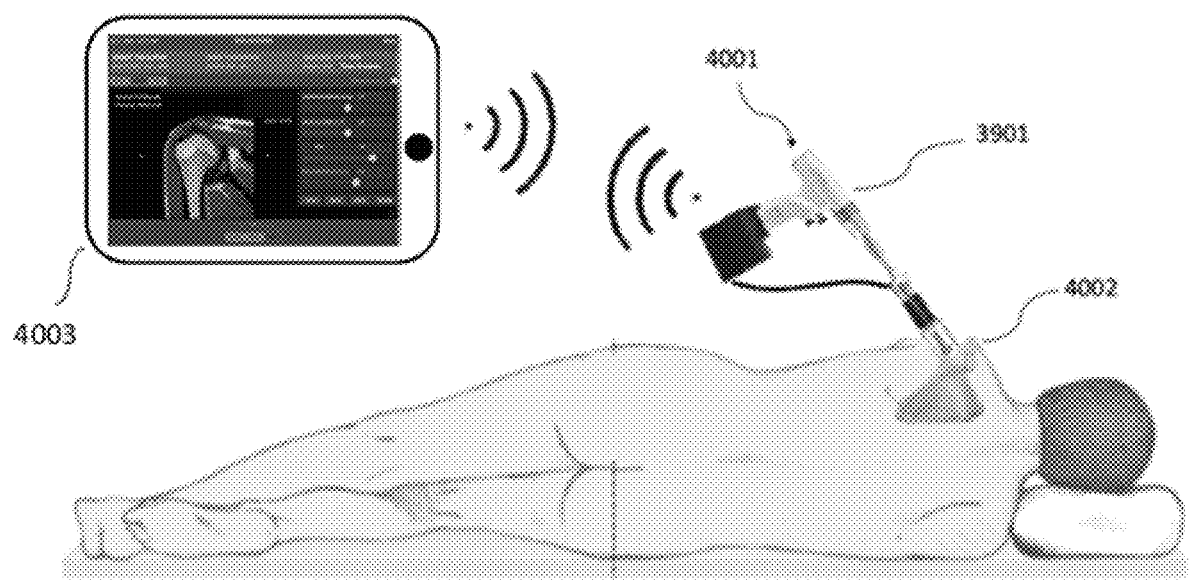
FIG. 39 is an illustration of a patient undergoing shoulder replacement surgery using a bone-mounted robot and hand-held power tool with a robot feedback controller communicating with a computer.

FIG. 39 illustrates a patient undergoing shoulder replacement surgery in 4001. The bone mounted hexapod robotic system 3901 is mounted on the shoulder for reaming the glenoid bone 4002. In this example, the robotic-assisted surgical system 4001 is communicating in real-time with a computer 4003 wirelessly. This allows the operating surgeon to make adjustments in real-time using the surgical planning software as described in FIG. 27. Also, real-time data or warnings can also be displayed on the computer alerting the surgeon of any deviations as well as providing real-time tool-path information as not to over ream the acetabulum cup. As mentioned above, the position and orientation of the component can be determined pre-operatively using the imaging data from the patient's shoulder. Once registration is complete using the customized glenoid registration guide, any changes to the implant position can be done using the surgical planning software 4003. For example, the customized glenoid registration guide can be designed manufactured for the default component orientation. Just prior to or during the procedure, the surgeon can make changes to the component position in all 6 DOF as long as it's within the robot's workspace.

Figure 40:
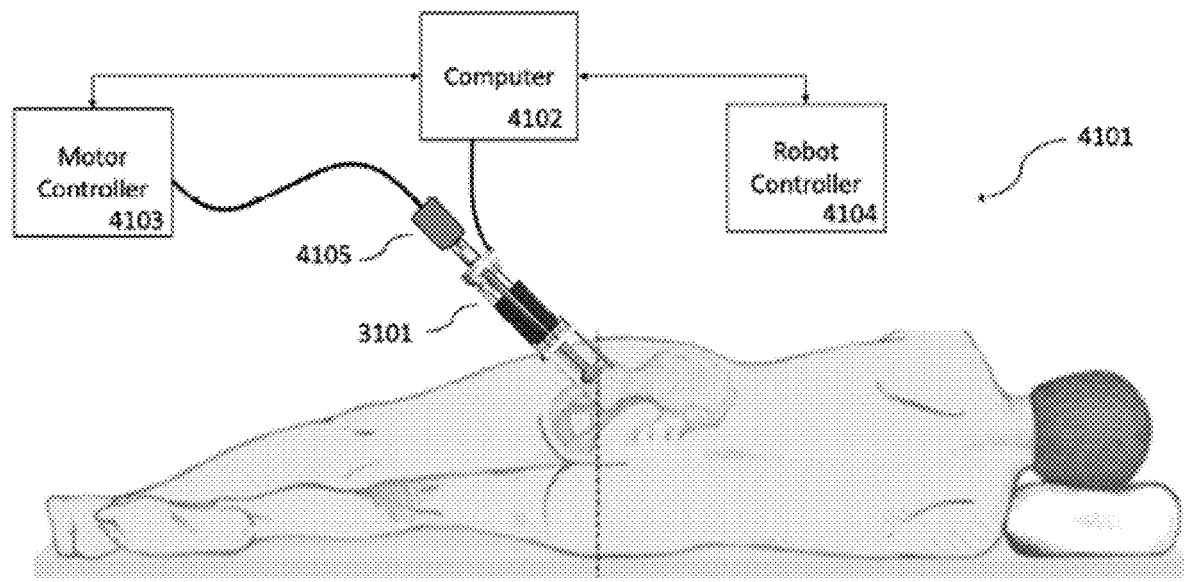
FIG. 40 is an illustration of a patient undergoing hip replacement surgery using a bone-mounted robot with a closed-loop system for milling an acetabulum.

FIG. 40 illustrates one embodiment of a 6 DOF hexapod robot 3101 mounted to the patient's pelvis for milling the acetabulum automatically following a pre-determined tool-path based on the implant shape described in FIG. 38. As discussed above, the intelligent robotic control system in FIG. 36 uses the output of the sensor 3501 as feedback for both force and position control in 4104. Also, the acetabular reamer is connected to a motor 4105 attached to the top plate of the robot in 3101. The torque/force sensor data can be used to control the motor in 4105. The data can be shared between 4103 and 4104 through the computer 4102 in a hierarchy decision-making structure. For example, when reaming hard or soft bone, the accuracy depends on the speed (RPM) of the tool and feed rate (tool-path motion). The tool's RPM is controlled by the motor controller 4105 and feed rate by the robot controller. In this example, the computer 4102 coordinates between the motor controller 4103 and robot controller 4104 to optimize the accuracy and time to complete the milling process. The optimization algorithm can reside locally on the computer in the form of software programs or remotely by network computing using cellular, wireless, or wired communication.

Figure 41:
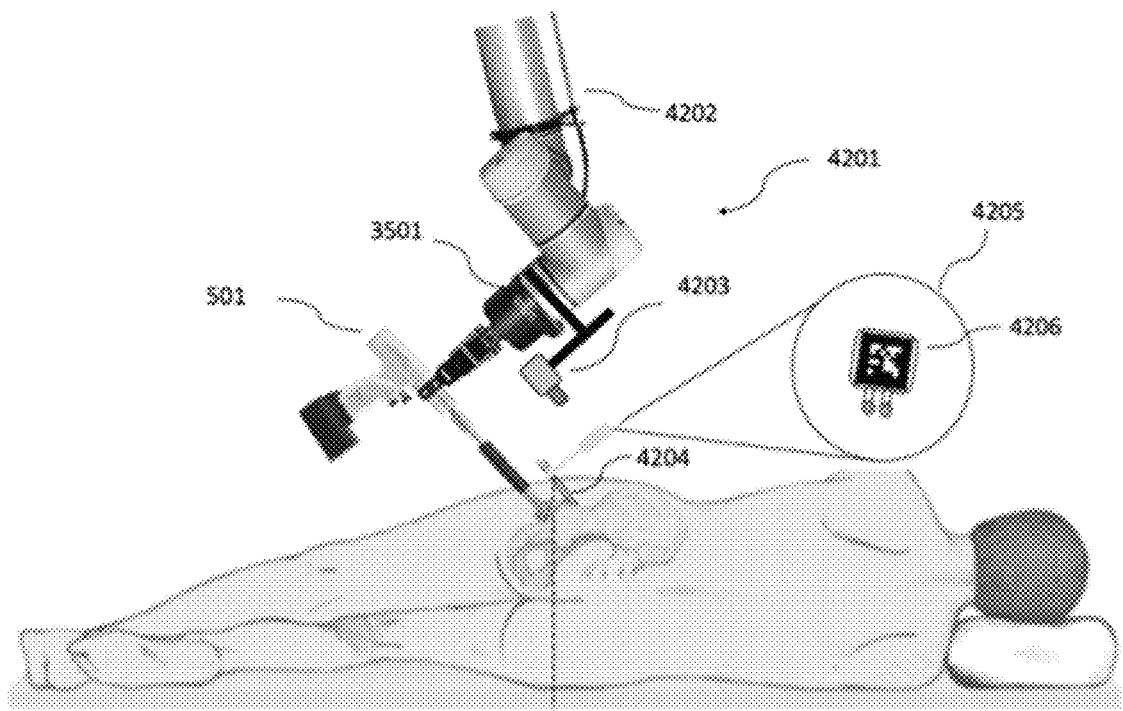
FIG. 41 is an illustration of a patient undergoing hip replacement surgery using a robotic arm and vision system for patient registration, tracking, and tool path planning using a two-dimensional marker.

FIG. 41 illustrates one embodiment 4201 of a free-standing 6 DOF robot 4202 with a force/torque sensor 3501 attached to the end-effector along with a force sensor 3501 and a gripper holding a power drill 501 for reaming the acetabulum. Also, attached to the robot is a vision/camera system 4203 for patient tracking, toolpath, and position control, and motion detection using a 2D marker 4206 mounted to the pins 4204 from the customized acetabulum registration. The position and orientation of the camera/vision system are known and calibrated for the robot's configuration. The 2D marker 4205 is similar to a QR or bar code 4206 for ease of recognition and differentiated from the surrounding objects within the field of view of the vision/camera system. Vision systems are similar to computer navigation systems in that they both require a line of sight between the camera (visible or infrared) and sensor/optical marker/electromagnetic.

Figure 42:
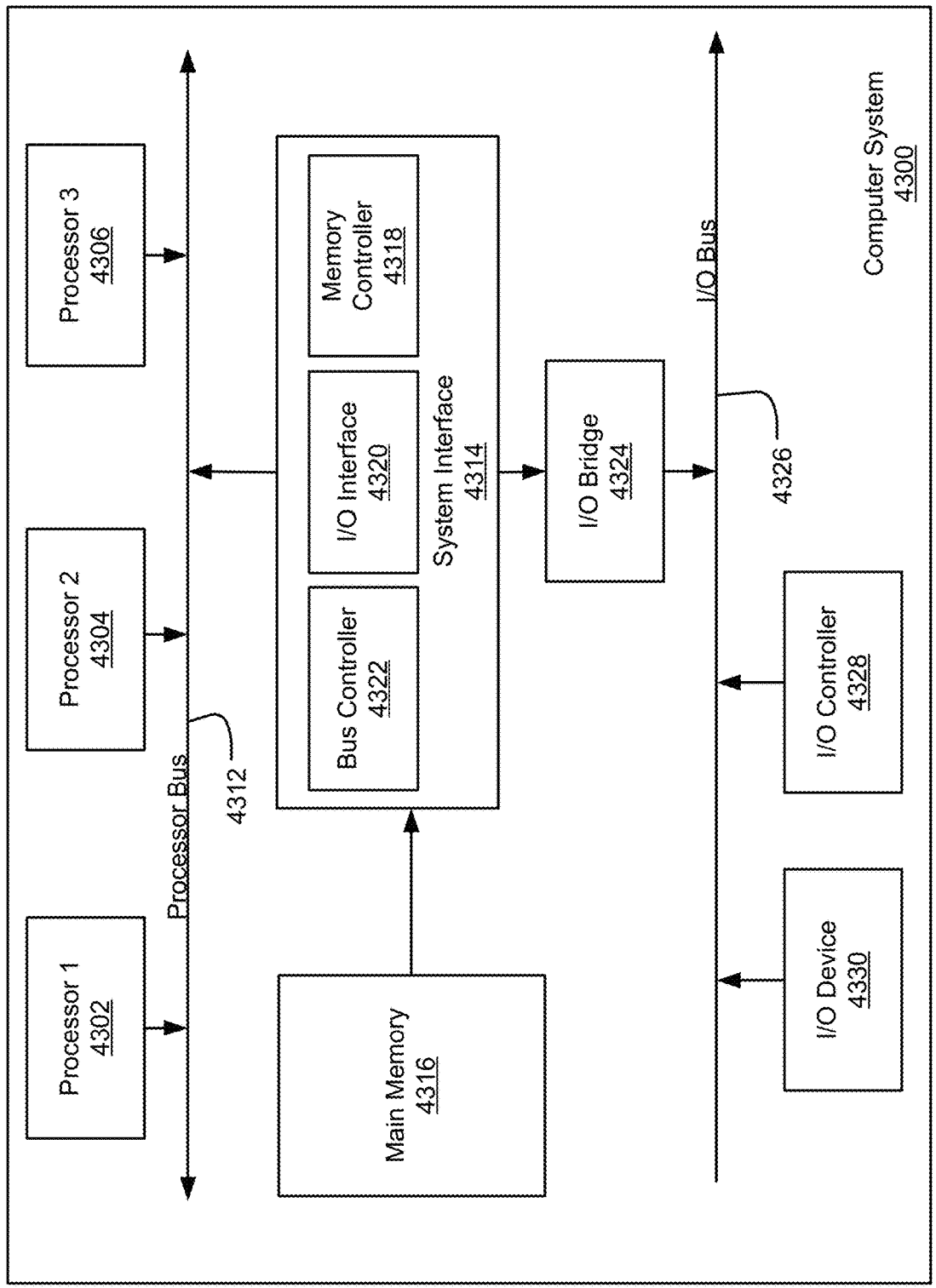
FIG. 42 is a diagram illustrating an example of a computing system which may be used in implementing embodiments of the present disclosure.

FIG. 42 is a block diagram illustrating an example of a computing device or computer system 4300 which may be used in implementing the embodiments of the components of the network disclosed above. For example, the computing system 4300 of FIG. 42 may be the computer 4102 of FIG. 40 discussed above. The computer system (system) includes one or more processors 4302-4306. Processors 4302-4306 may include one or more internal levels of cache (not shown) and a bus controller or bus interface unit to direct interaction with the processor bus 4312. Processor bus 4312, also known as the host bus or the front side bus, may be used to couple the processors 4302-4306 with the system interface 4314. System interface 4314 may be connected to the processor bus 4312 to interface other components of the system 4300 with the processor bus 4312. For example, system interface 4314 may include a memory controller 4318 for interfacing a main memory 4316 with the processor bus 4312. The main memory 4316 typically includes one or more memory cards and a control circuit (not shown). System interface 4314 may also include an input/output (I/O) interface 4320 to interface one or more I/O bridges or I/O devices with the processor bus 4312. One or more I/O controllers and/or I/O devices may be connected with the I/O bus 4326, such as I/O controller 4328 and I/O device 4330, as illustrated.

I/O device 4330 may also include an input device (not shown), such as an alphanumeric input device, including alphanumeric and other keys for communicating information and/or command selections to the processors 4302-4306. Another type of user input device includes cursor control, such as a mouse, a trackball, or cursor direction keys for communicating direction information and command selections to the processors 4302-4306 and for controlling cursor movement on the display device.

System 4300 may include a dynamic storage device, referred to as main memory 4316, or a random access memory (RAM) or other computer-readable devices coupled to the processor bus 4312 for storing information and instructions to be executed by the processors 4302-4306. Main memory 4316 also may be used for storing temporary variables or other intermediate information during execution of instructions by the processors 4302-4306. System 4300 may include a read only memory (ROM) and/or other static storage device coupled to the processor bus 4312 for storing static information and instructions for the processors 4302-4306. The system set forth in FIG. 42 is but one possible example of a computer system that may employ or be configured in accordance with aspects of the present disclosure.

According to one embodiment, the above techniques may be performed by computer system 4300 in response to processor 4304 executing one or more sequences of one or more instructions contained in main memory 4316. These instructions may be read into main memory 4316 from another machine-readable medium, such as a storage device. Execution of the sequences of instructions contained in main memory 4316 may cause processors 4302-4306 to perform the process steps described herein. In alternative embodiments, circuitry may be used in place of or in combination with the software instructions. Thus, embodiments of the present disclosure may include both hardware and software components.

A machine readable medium includes any mechanism for storing or transmitting information in a form (e.g., software, processing application) readable by a machine (e.g., a computer). Such media may take the form of, but is not limited to, non-volatile media and volatile media and may include removable data storage media, non-removable data storage media, and/or external storage devices made available via a wired or wireless network architecture with such computer program products, including one or more database management products, web server products, application server products, and/or other additional software components. Examples of removable data storage media include Compact Disc Read-Only Memory (CD-ROM), Digital Versatile Disc Read-Only Memory (DVD-ROM), magneto-optical disks, flash drives, and the like. Examples of non-removable data storage media include internal magnetic hard disks, SSDs, and the like. The one or more memory devices 4306 may include volatile memory (e.g., dynamic random access memory (DRAM), static random access memory (SRAM), etc.) and/or non-volatile memory (e.g., read-only memory (ROM), flash memory, etc.).

Computer program products containing mechanisms to effectuate the systems and methods in accordance with the presently described technology may reside in main memory 516, which may be referred to as machine-readable media. It will be appreciated that machine-readable media may include any tangible non-transitory medium that is capable of storing or encoding instructions to perform any one or more of the operations of the present disclosure for execution by a machine or that is capable of storing or encoding data structures and/or modules utilized by or associated with such instructions. Machine-readable media may include a single medium or multiple media (e.g., a centralized or distributed database, and/or associated caches and servers) that store the one or more executable instructions or data structures.

It should be noted that the flowcharts above are illustrative only. Alternative embodiments of the present invention may add operations, omit operations, or change the order of operations without affecting the spirit and scope of the present invention. The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

Embodiments of the present disclosure include various steps, which are described in this specification. The steps may be performed by hardware components or may be embodied in machine-executable instructions, which may be used to cause a general-purpose or special-purpose processor programmed with the instructions to perform the steps. Alternatively, the steps may be performed by a combination of hardware, software and/or firmware.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations together with all equivalents thereof.

What is claimed:

1. A system for performing a surgical arthroplasty procedure, the system comprising:
a configurable bone-mounted robotic device configured to be attached to an anterior inferior iliac spine of a patient's anatomy via at least one guide pin,
a drill guide of a customized registration guide comprising: a circular portion, a triangular portion extending from the circular portion, an elliptical mating feature extending from the triangular portion and configured for contacting the patient's anatomy at a junction of a pubis and ilium near the anterior inferior iliac spine to prevent the guide from rotating during joint arthroplasty procedure when mated, and at least three cylindrical mating shapes extending from the circular portion and configured to contact with a rim of an acetabular portion of the patient's anatomy when mated;
wherein an orientation of the guide pin relative to the anterior inferior iliac of the patient's anatomy is based on the drill guide of the customized registration guide defining an oriented workspace for the surgical arthroplasty procedure and generated from locating a plurality of landmark locations within a plurality of two-dimensional images of the patient's anatomy, the plurality of landmark locations defining the oriented workspace for the surgical arthroplasty procedure;
an acetabular reamer connected to a motor controlled by a motor controller and positioned within the oriented workspace for the surgical arthroplasty procedure by the configurable bone-mounted robotic device;
a force sensor in mechanical communication with the acetabular reamer; and
a computing device comprising:
at least one processing device; and
a non-transitory memory device in communication with the at least one processing device for storing one or more instructions that, when executed by the at least one processing device, cause the computing device to:
receive force information from the force sensor; and
adjust, based on the received force information, a position of the configurable bone-mounted robotic device and thereby a position of the acetabular reamer relative to the oriented workspace.

2. The system of claim 1, wherein the force sensor is a torque sensor and the information indicates a torque force of the acetabular reamer on a portion of the patient's anatomy.

3. The system of claim 2, wherein the one or more instructions further cause the computing device to adjust a rotations-per-minute (RPM) of the acetabular reamer based on the information indicating the torque force of the acetabular reamer on the portion of the patient's anatomy.

4. The system of claim 1, wherein the force sensor is a torque sensor determining a torque force of the acetabular reamer, and wherein adjusting the position of the bone-mounted robotic device is further based on the determined torque force received from the torque sensor.

5. The system of claim 1, wherein the configurable bone-mounted robotic device comprises a hexapod robotic device with six degrees of freedom, the hexapod robotic device comprising a base plate, top plate, and a plurality of prismatic joints between the base plate and the top plate.

6. The system of claim 5, wherein the acetabular reamer passes through the base plate and the top plate of the hexapod robotic device along a reaming axis defined by the oriented workspace for the surgical arthroplasty procedure.

7. The system of claim 5, wherein the plurality of prismatic joints attach to the base plate at a first end in pairs via a connector joint, the connector joint one of a universal joint, a spherical joint, or a ball joint.

8. The system of claim 7, wherein the plurality of prismatic joints attach, at a second end opposite the first end, to the top plate via a universal joint.

9. The system of claim 5, wherein the base plate comprises a center slot through which the acetabular reamer is inserted during the surgical arthroplasty procedure.

10. The system of claim 1, wherein the computing device is further caused to: adjust a speed of the acetabular reamer based on the received force information.

11. The system of claim 1, wherein the computing device is further caused to: adjust a position of the acetabular reamer based on the received force information.

12. The system of claim 1, wherein the customized registration guide further comprises one or more drill hole guides extending outward from the triangular portion.

13. The system of claim 1, wherein a first of the at least three mating shapes of the customized registration guide configured to contact a pubic portion of the rim of the acetabular portion, a second of the at least three mating shapes of the customized registration guide configured to contact an ischial portion of the rim of the acetabular portion, and a third of the at least three mating shapes of the customized registration guide configured to contact an ischium portion of the rim of the acetabular portion.

14. The system of claim 1, wherein the customized registration guide comprises a femoral resection guide for mating to a femoral head of the anatomy of the patient during the surgical arthroplasty procedure.

15. The system of claim 1, further comprising: a vision system tracking a path of the acetabular reamer and transmitting tracking information to the computing device, wherein the computing device adjusts the position of the bone-mounted robotic device based further on the transmitted tracking information.

* * * * *